US012708611B2

(12) United States Patent
Laperle et al.

(10) Patent No.: US 12,708,611 B2
(45) Date of Patent: Aug. 18, 2026

(54) DIAGNOSTIC AND DRUG SCREENING FOR MOLECULAR SIGNATURES OF EARLY ONSET SPORADIC PARKINSON'S DISEASE

(71) Applicant: CEDARS-SINAI MEDICAL CENTER, Los Angeles, CA (US)

(72) Inventors: Alexander Laperle, North Hollywood, CA (US); Samuel Sances, Santa Monica, CA (US); Nur Yucer, Los Angeles, CA (US); Clive N. Svendsen, Pacific Palisades, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1078 days.

(21) Appl. No.: 17/043,272

(22) PCT Filed: Apr. 5, 2019

(86) PCT No.: PCT/US2019/026195

§ 371 (c)(1),
(2) Date: Sep. 29, 2020

(87) PCT Pub. No.: WO2019/212691

PCT Pub. Date: Nov. 7, 2019

(65) Prior Publication Data

US 2021/0033628 A1 Feb. 4, 2021

Related U.S. Application Data

(60) Provisional application No. 62/816,795, filed on Mar. 11, 2019, provisional application No. 62/755,365, filed on Nov. 2, 2018, provisional application No. 62/664,942, filed on May 1, 2018, provisional application No. 62/664,888, filed on Apr. 30, 2018, provisional application No. 62/664,827, filed on Apr. 30, 2018.

(51) Int. Cl.

| | |
|---|---|
| ***A61P 25/16*** | (2006.01) |
| ***A61K 31/22*** | (2006.01) |
| ***A61K 35/545*** | (2015.01) |
| ***C12N 5/074*** | (2010.01) |
| ***C12N 5/10*** | (2006.01) |
| ***C12N 15/11*** | (2006.01) |
| ***G01N 33/50*** | (2006.01) |
| ***G01N 33/68*** | (2006.01) |

(52) U.S. Cl.

CPC ............ *A61K 31/22* (2013.01); *A61K 35/545* (2013.01); *A61P 25/16* (2018.01); *C12N 5/0696* (2013.01); *C12N 5/10* (2013.01); *C12N 15/111* (2013.01); *G01N 33/5008* (2013.01); *G01N 33/6896* (2013.01); *G01N 2333/4704* (2013.01)

(58) Field of Classification Search

CPC ......... A61K 35/545; A61P 25/16; C12N 5/10; G01N 33/5008

See application file for complete search history.

(56) References Cited

U.S. PATENT DOCUMENTS

| | | |
|---|---|---|
| 6,300,080 B1 | 10/2001 | Brenner et al. |
| 7,989,197 B2 | 8/2011 | Yoo et al. |
| 8,647,861 B2 | 2/2014 | Ingber et al. |
| 9,236,212 B2 | 1/2016 | Tanaka |
| 9,790,470 B2 | 10/2017 | Vallier et al. |
| 10,174,289 B2 | 1/2019 | Wells et al. |
| 11,326,149 B2 | 5/2022 | Kerns et al. |
| 2004/0247571 A1 | 12/2004 | Meijer et al. |
| 2007/0077649 A1 | 4/2007 | Sammak et al. |
| 2007/0128722 A1 | 6/2007 | Lin |
| 2007/0281353 A1 | 12/2007 | Vacanti et al. |

(Continued)

FOREIGN PATENT DOCUMENTS

| | | |
|---|---|---|
| AU | 2015204375 A1 | 8/2015 |
| AU | 2016341880 A1 | 5/2018 |

(Continued)

OTHER PUBLICATIONS

Cell Signaling Technology "Certificate of Analysis" for Product No. 9375, Phospho-PKC alpha/beta II (Thr638/641) antibody, Sep. 5, 2019. (Year: 2019).*

(Continued)

*Primary Examiner* — Aurora M Fontainhas
*Assistant Examiner* — Jennifer A Benavides
(74) *Attorney, Agent, or Firm* — Nixon Peabody LLP

(57) ABSTRACT

Induced Pluripotent Stem Cell (Ipsc) technology enables the generation and study of living brain tissue relevant to Parkinson's disease (PD) ex vivo. Utilizing cell lines from PD patients presents a powerful discovery system that links cellular phenotypes observed in vitro with real clinical data. Differentiating patient-derived iPSCs towards a dopaminergic (DA) neural fate revealed that these cells exhibit molecular and functional properties of DA neurons in vitro that are observed to significantly degenerate in the substantia nigra of PD patients. Clinical symptoms that drive the generation of other relevant cell types may also yield novel PD-specific phenotypes in vitro that have the potential to lead to new therapeutic avenues for patients with PD. Due to their early onset and non-familial origin, differentiated nervous tissue from these patients offer a key opportunity to discover neuron subtype-specific pathological mechanisms and importantly interrogate the contribution of their genetic background in susceptibility to PD.

10 Claims, 15 Drawing Sheets

(56) References Cited

U.S. PATENT DOCUMENTS

2008/0044847 A1 2/2008 Shusta et al.
2008/0132445 A1 6/2008 Ormandy et al.
2008/0305086 A1 12/2008 Poole
2009/0075374 A1 3/2009 Palecek et al.
2009/0123383 A1 5/2009 Frangioni
2009/0214649 A1 8/2009 Gazit et al.
2009/0258337 A1 10/2009 Yagi
2009/0317852 A1 12/2009 Parker et al.
2009/0324559 A1 12/2009 Sakurada et al.
2010/0136690 A1 6/2010 Sundstorm et al.
2011/0064700 A1 3/2011 Cardozo et al.
2011/0097796 A1 4/2011 Loa
2011/0111499 A1 5/2011 Torihashi
2011/0245307 A1 10/2011 Alkon
2011/0250585 A1 10/2011 Ingber et al.
2012/0094381 A1 4/2012 Chambers et al.
2012/0107934 A1 5/2012 Poole
2012/0128655 A1 5/2012 Kim et al.
2012/0171354 A1 7/2012 O'Neill et al.
2012/0196312 A1 8/2012 Sato et al.
2012/0211373 A1 8/2012 El-Sayed et al.
2013/0137130 A1 5/2013 Wells et al.
2013/0224857 A1 8/2013 Blak et al.
2013/0280802 A1 10/2013 Schulz et al.
2013/0288969 A1 10/2013 Scadden
2014/0038279 A1 2/2014 Ingber et al.
2014/0065660 A1 3/2014 Kim et al.
2014/0093905 A1 4/2014 Ingber et al.
2014/0134732 A1 5/2014 Ashton
2014/0142370 A1 5/2014 Wong et al.
2014/0171380 A1 6/2014 Kim et al.
2014/0199700 A1 7/2014 Kume et al.
2014/0248621 A1 9/2014 Collins
2014/0288093 A1 9/2014 Krainc et al.
2014/0315990 A1 10/2014 Alkon et al.
2014/0329321 A1 11/2014 Rajesh et al.
2014/0342445 A1 11/2014 Ingber et al.
2015/0017674 A1 1/2015 Christensen et al.
2015/0023928 A1 1/2015 Hassiotou
2015/0037320 A1 2/2015 McGrath et al.
2015/0071874 A1 3/2015 Han et al.
2015/0151011 A1 6/2015 Jang et al.
2015/0218522 A1 8/2015 Peterson et al.
2015/0232810 A1 8/2015 Luo et al.
2015/0252328 A1 9/2015 Woodruff et al.
2015/0258124 A1 9/2015 Katajisto et al.
2015/0265652 A1 9/2015 George et al.
2015/0329828 A1 11/2015 Rezania
2016/0145642 A1 5/2016 Cui et al.
2016/0152950 A1 6/2016 Zhang et al.
2016/0340633 A1 11/2016 Davis et al.
2017/0107498 A1 4/2017 Sareen et al.
2017/0226478 A1 8/2017 Kerns et al.
2017/0240866 A1 8/2017 Wells et al.
2017/0253856 A1 9/2017 Douvaras et al.
2017/0283772 A1 10/2017 Qian et al.
2017/0292116 A1 10/2017 Erlls et al.
2017/0313976 A1 11/2017 Kuwahara et al.
2018/0021383 A1 1/2018 George et al.
2018/0057788 A1 3/2018 Kerns et al.
2018/0237741 A1 8/2018 Gazit et al.
2018/0298331 A1 10/2018 Kerns et al.
2018/0298332 A1 10/2018 Kerns et al.
2018/0305651 A1 10/2018 Kerns et al.
2018/0305668 A1 10/2018 Gazit et al.
2019/0009270 A1 1/2019 Gazit et al.
2019/0018000 A1 1/2019 Gazit et al.
2019/0031992 A1 1/2019 Kerns et al.
2019/0153395 A1 5/2019 Barrett et al.
2019/0194606 A1 6/2019 Vatine et al.
2019/0359924 A1 11/2019 Kerns et al.
2020/0000267 A1 1/2020 Zuidervaart et al.
2020/0002671 A1 1/2020 Qu et al.
2020/0032215 A1 1/2020 Svendsen et al.
2020/0071673 A1 3/2020 Sareen et al.
2020/0157508 A1 5/2020 Barrett et al.
2021/0000880 A1 1/2021 Svendsen et al.
2021/0023039 A1 1/2021 Laperle et al.
2021/0024886 A1 1/2021 Laperle et al.
2021/0033628 A1 2/2021 Laperle et al.
2021/0130774 A1 5/2021 Sances et al.
2023/0159896 A1 5/2023 Sharma et al.
2023/0333092 A1 10/2023 Sances et al.
2024/0067933 A1 2/2024 Laperle et al.
2024/0076629 A1 3/2024 Laperle et al.
2025/0057887 A1 2/2025 Svendsen et al.

FOREIGN PATENT DOCUMENTS

AU 2017213795 A1 8/2018
AU 2017214468 A1 9/2018
AU 2017319168 A1 3/2019
AU 2017321489 A1 3/2019
AU 2018235950 A1 10/2019
AU 2018236273 A1 10/2019
AU 2018270270 A1 12/2019
AU 2017319168 B2 4/2021
AU 2016341880 B2 5/2021
CA 3002399 A1 4/2017
CA 3013337 A1 8/2017
CA 3013357 A1 8/2017
CA 3034614 A1 3/2018
CA 3035058 A1 3/2018
CA 3055992 A1 9/2018
CA 3056089 A1 9/2018
CA 3064086 A1 11/2018
CN 109642212 A 4/2019
EP 3008168 A1 4/2016
EP 3031908 A1 6/2016
EP 3365424 A0 8/2018
EP 3411470 A2 12/2018
EP 3411472 A1 12/2018
EP 3503901 A1 7/2019
EP 3504319 A1 7/2019
EP 3625331 A1 3/2020
EP 3768823 1/2021
EP 3775161 2/2021
EP 3787613 3/2021
EP 3787649 A1 3/2021
EP 4217114 A0 8/2023
GB 2561312 A 10/2018
GB 2562406 A 11/2018
GB 2564582 A 1/2019
GB 2568446 A 5/2019
GB 2569058 A 6/2019
GB 2574988 A 12/2019
GB 2575574 A 1/2020
GB 2561312 B 3/2021
GB 2564582 B 9/2021
HK 1260726 B2 7/2021
JP 2003-511346 9/2000
JP 2013-537553 A 10/2013
JP 2014-171434 9/2014
JP 2014-171434 A 9/2014
JP 2014-528247 A 10/2014
JP 2015-504427 A 2/2015
JP 2015-504676 A 2/2015
JP 2015504676 2/2015
JP 2018533940 A 11/2018
JP 2019506861 A 3/2019
JP 2021-520784 A 8/2021
JP 2021-523700 A 9/2021
JP 2021-523888 A 9/2021
KR 20180069882 A 6/2018
SG 11201803143Y A 5/2018
SG 11201901621V A 3/2019
SG 11201901628X A 3/2019
SG 11201908358P A 10/2019
SG 11201908359U A 10/2019
WO 2000053218 9/2000
WO 2005021720 A2 3/2005
WO WO 2010009307 A2 1/2010
WO WO 2010/108005 A2 9/2010
WO WO-2011109440 A1 * 9/2011 ................ A61P 1/16

(56) References Cited

FOREIGN PATENT DOCUMENTS

| | | | |
|---|---|---|---|
| WO | 2012/100084 | A1 | 7/2012 |
| WO | WO 2012/118799 | A2 | 9/2012 |
| WO | 2013/056216 | A1 | 4/2013 |
| WO | 2013/071282 | A1 | 5/2013 |
| WO | WO 2013/065763 | A1 | 5/2013 |
| WO | 2013/086486 | A1 | 6/2013 |
| WO | 2013108926 | A1 | 7/2013 |
| WO | WO2013106677 | A1 | 7/2013 |
| WO | 2013/184193 | A1 | 12/2013 |
| WO | WO 2014/172682 | A1 | 10/2014 |
| WO | WO 2014/176606 | A1 | 10/2014 |
| WO | WO 2014159356 | A1 | 10/2014 |
| WO | WO 2015/052143 | A1 | 4/2015 |
| WO | WO 2015/057261 | A1 | 4/2015 |
| WO | WO 2015/126528 | A1 | 8/2015 |
| WO | 2015143342 | A1 | 9/2015 |
| WO | WO 2015/138032 | A2 | 9/2015 |
| WO | WO 2015/138034 | A2 | 9/2015 |
| WO | WO 2015/163823 | A1 | 10/2015 |
| WO | WO 2015153451 | A1 | 10/2015 |
| WO | WO 2015/181253 | A1 | 12/2015 |
| WO | WO 2015/183920 | A2 | 12/2015 |
| WO | WO 2015/188131 | A1 | 12/2015 |
| WO | 2016063985 | A1 | 4/2016 |
| WO | WO 2016061464 | A1 | 4/2016 |
| WO | WO 2016/086040 | A1 | 6/2016 |
| WO | WO 2016/093222 | A | 6/2016 |
| WO | 2016/141137 | A1 | 9/2016 |
| WO | 2016162747 | A2 | 10/2016 |
| WO | 2016183252 | A1 | 11/2016 |
| WO | WO 2017/035119 | A1 | 3/2017 |
| WO | 2017070224 | A1 | 4/2017 |
| WO | 2017075271 | A1 | 5/2017 |
| WO | 2017078807 | A1 | 5/2017 |
| WO | 2017/112455 | A1 | 6/2017 |
| WO | WO 2017/123806 | A1 | 7/2017 |
| WO | WO 2017/136462 | A2 | 8/2017 |
| WO | WO 2017/136479 | A1 | 8/2017 |
| WO | WO 2017/143049 | A1 | 8/2017 |
| WO | WO 2017/200486 | A1 | 11/2017 |
| WO | 2017/219000 | A1 | 12/2017 |
| WO | 2018/035214 | A1 | 2/2018 |
| WO | WO 2018/044885 | A1 | 3/2018 |
| WO | WO 2018/044934 | A1 | 3/2018 |
| WO | 2018106628 | A1 | 6/2018 |
| WO | 2018/140647 | A1 | 8/2018 |
| WO | 2018/176001 | A1 | 9/2018 |
| WO | 2018175574 | A1 | 9/2018 |
| WO | WO 2018/170139 | A1 | 9/2018 |
| WO | WO 2018/170180 | A1 | 9/2018 |
| WO | WO 2018/213773 | A1 | 11/2018 |
| WO | 2019023793 | A1 | 2/2019 |
| WO | 2019/122291 | A2 | 6/2019 |
| WO | 2019169351 | A1 | 9/2019 |
| WO | 2019178164 | A1 | 9/2019 |
| WO | 2019178550 | A1 | 9/2019 |
| WO | WO 2019/183597 | A1 | 9/2019 |
| WO | 2019195798 | A1 | 10/2019 |
| WO | 2019195800 | A1 | 10/2019 |
| WO | 2019212690 | A1 | 11/2019 |
| WO | 2019212691 | A1 | 11/2019 |
| WO | 2021/081229 | A1 | 4/2021 |
| WO | 2021/081237 | A1 | 4/2021 |
| WO | 2021222724 | A1 | 11/2021 |
| WO | 2022066723 | A1 | 3/2022 |

OTHER PUBLICATIONS

Newton AC. Protein kinase C: structural and spatial regulation by phosphorylation, cofactors, and macromolecular interactions. Chem Rev. Aug. 2001;101(8):2353-64. (Year: 2001).*

Laperle AH et al. iPSC modeling of young-onset Parkinson's disease reveals a molecular signature of disease and novel therapeutic candidates. Nat Med. Feb. 2020;26(2):289-299. (Year: 2020).*

EP 19782199.4 Partial Supplementary Search Report dated Nov. 30, 2021, 15 pages.

EP 19796470.3 European Extended Search Report dated Dec. 10, 2021, 11 pages.

Burkhardt et al., A Cellular Model for Sporadic ALS using Patient-Derived Induced Pluripotent Stem Cells, Molecular and Cellular Neuroscience, 2013, vol. 56, pp. 355-364.

Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.

Lenzi et al., Differentiation of Control and ALS Mutant Human iPSCs into Functional Skeletal Muscle Cells, A Tool for the Study of Neuromuscolar Diseases, Stem Cell Research, 2016, vol. 17, pp. 140-147.

Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.

Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.

International Search Report and Written Opinion of PCT/US2019/26178, Dated Jun. 11, 2019, 14 Pages.

International Search Report and Written Opinion of PCT/US2019/26183, Dated Jun. 12, 2019, 10 Pages.

International Search Report and Written Opinion of PCT/US2019/026195 Jun. 12, 2019, 10 pages.

International Search Report and Written Opinion of PCT/US2019/026193 Jul. 1, 2019, 8 pages.

Kondo, T. et al., Ipsc-based Coound screening and in vitro trials identify a synergistic anti-amyloid b combination for Alzheimer's Disease, Cell Reports, 2017, vol. 21, pp. 2304-2312.

McKinney, C.E. et al., Using induced pluripotent stem cells derived neurons to model brain diseases, Neural Regeneration Research, 2017, 12:7 pp. 1-11.

Li, Y. et al., Protein kinase C controls lysosome biogenesis independently of mTORC1, Nature Cell Biology, 2016, 10:10, pp. 1-26.

Kilpatrick, K. et al., Genetic and chemical activation of TFEB mediates clearance of aggregated a-synuclein, PLoS One, 2015, 10:3, pp. 1-21.

Chou, B.K. et al., Efficient human iPS cell derivation by a non-integrating plasmid from blood cells with unique epigenetic and gene expression signatures, Cell Research, 2011, 21:3, pp. 518-529.

Sundberg, m. et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.

Arendt et al., Form and Function: how Estrogen and Progesterone Regulate the Mammary Epithelial Hierarchy, J. Mammary Gland Biol Neoplasia, 2015, 20:9-25.

Qiao et al, AP2y regulates neural and epiderman development downstream of the BMP pathway at early stages of ectodermal patterning, Cell Research, 2012, 22:1546-1561.

Lin et al., Embryoid body formation from human pluripotent stem cells in chemically defined E8 media, StemBook, ed, Jun. 1, 2014.

JP Reasons for Rejection-2020-560893 dated Feb. 6, 2023, 9 pages.

Matsumoto et al., Functional neurons generated from T Cell-derived induced pluripotent stem cells for neurological disease modeling, 2016, 6:422-435.

Moors et al., Therapeutic potential of autophagy-enhancing agents in Parkinson's disease, Molecular Neurodegeneration, 2017, 12:11, p. 1-18.

Okita et al., An efficient nonviral method to generate integration-free human-induced pluripotent stem cells from cord blood and peripheral blood cells, Stem Cells 2013, 31:458-466.

Kondo et al., iPSC-Based compound screening and in vitro trials identify a synergistic anti-amyloid B combination for Alzheimer's Disease, Cell Reports 2017, 21:2304-2312.

Hojo et al., Development of high-throughput screening system for osteogenic drugs using a cell-based sensor, Biochemical and Biophysical Research Communiatins 376(2):375-379, 2008.

(56) References Cited

OTHER PUBLICATIONS

Hayes et al., Strategies to generate induced pluripotentstem cells, Methods in Molecular Biology 1029: 77-92. doi: 10.1007/978-1-62703-478-4_6 (Year: 2013).
Shafa et al., Human-Induced Pluripotent Stem Cells Manufactured Using a Current Good Manufacturing Practice-Compliant Process Differentiate Into Clinically Relevant Cells From Three Germ Layers, Frontiers in Medicine 5: 69. doi: 10.3389/fmed.
Ionescu et al., Compartmental microfluidic system for studying muscle-neuron communication and neuromuscular junction maintenance, 2016 European Journal of Cell Biology, 95:69-88.
DMEM F-12 Formulation, pp. 1-5, 2022.
Mehta et al., The actions of retinoids on cellular growth correlate with their actions on gap junctional communication, JCB 108, 1053-1065, 1989.
Essential 8 medium C037161 Essential8System Brochure (thermofisher.com), downloaded on Aug. 24, 2022, pp. 1-2.
ISR and WO for PCT/US2021/030128 mailed Aug. 25, 2021, 10 pages.
Kim, et al. [3-Cell regeneration through the transdifferentiation of pancreatic cells: Pancreatic progenitor cells in the pancreas, Journal of Diabetes Investigation 7(3): 286-296. doi: 10.1111/jdi .12475. (Year: 2016).
Clayton, et al., Generating induced pluripotent stem cell derived endothelial cells and induced endothelial cells for cardiovascular disease modelling and therapeutic angiogenesis, International Journal of Cardiology 197: 116-122. doi: 10.1016/ j.ijcard.2015.06.038. (Year: 2015).
Munera et al., Differentiation of Human Pluripotent Stem Cells into Colonic Organoids via Transient Activation of BMP Signaling, Cell Stem Cell, 21, 51-64, 2017.
International Search Report and Written Opinion for PCT/US2018/015318 May 2, 2018, 16 pages.
International Search Report and Written Opinion for PCT/US2018/024198 dated Aug. 13, 2018, 15 pages.
International Search Report and Written Opinion for PCT/US2020/056896 dated Oct. 22, 2020, 11 pages.
International Search Report and Written Opinion for PCT/US2020/056906 dated Mar. 16, 2021, 13 pages.
International Preliminary Report on Patentability for PCT/US2018/015318 dated Jul. 30, 2019, 12 pages.
International Preliminary Report on Patentability for PCT/US2018/024198 dated Feb. 25, 2020, 12 pages.
EP 19782199.4 Extended European Search Report dated Mar. 3, 2022, 12 pages.
EP 19796911.6 Extended Search Report dated Apr. 29, 2022, 15 pages.
Akhtar et al., Inducible Expression of GDNF in Transplanted iPSC-Derived Nueral Progenitor Cells, Stem Cell Reports, 2018, vol. 10, pp. 1696-1704.
Araoka, et al., Efficient and rapid induction of human iPSCs/ESCs into nephrogenic intermediate mesoderm using small molecule-based differentiation methods, PLoS One, 2014, 9(1), 14 pages.
Badger et al., Parkinson's disease in a dish – Using stem cells as a molecular tool. Neuropharmacology, 2014, vol. 76, pp. 88-96.
Bai et al., BMP-2, VEGF and bFGF Synergistically Promote the Osteogenic Differentiation of Rat Bone Marrow-derived Mesenchymal Stem Cells, Biotechnol Lett, 2013, vol. 35, pp. 301-308.
Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.
Bohrsen et al. Supportive angiogenic and osteogenic differentiation of mesenchymal stromal cells and endothelial cells in monolayer and co-cultures. International Journal of Oral Science (2016) 8, 223-230 (Year: 2016).
Chen, et al., Chemically defined conditions for human iPSC derivation and culture, 2011, Nat. Methods, 8(5), 8 pages.
Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.
Farrelly et al., Extracellular matrix regulates apoptosis in mammary epithelium through a control on insulin signaling, The Journal of Cell Biology, 1999, 144(6):1337-1347.
Gurusamy et al., Hepatocyte Growth Factor-Like Protein is a Positive Regulator of Early Mammary Gland Ductal Morphogenesis, Mechanisms of Development, 2014, vol. 133, pp. 11-22.
Hens et al., BMP4 and PTHrP interact to stimulate ductal outgrowth during embryonic mammary development and to inhibit hair follicle induction, Development, 2017, 134:1221-1230.
Ichida et al., Probing disorders of the nervous system using reprogramming approaches, The EMBO Journal / European Molecular Biology Organization, 2015, vol. 34, No. 11, pp. 1456-1477.
Kessler et al., The Notch and Wnt pathways Regulate Stemness and Differentiation in Human Fallopian Tube Organoids, Nature Communications, 2015, vol. 6, p. 8989.
Kim et al. A practical guide to microfluidic perfusion culture of adherent mammalian cells. Lab Chip, 2007, 7, 681-694 (Year: 2007).
Kim et al. Shear Stress Induced by an Interstitial Level of Slow Flow Increases the Osteogenic Differentiation of Mesenchymal Stem Cells through TAZ Activation. PLoS One 9(3): e92427. p. 1-9 (Year: 2014).
Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).
Levanon, et al., Primary ex vivo cultures of human fallopian tube epithelium as a model for serous ovarian carcinogenesis, Oncogene, 2010, 29(8):1103-1113.
Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007) Abstract Only.
Nishimura et al. Effect of osteogenic differentiation medium on proliferation and differentiation of human mesenchymal stem cells in threedimensional culture with radial flow bioreactor. Regenerative Therapy 2 (2015) 24-31 (Year: 2015).
O'Neill et al., Genetic disorders coupled to ROS deficiency, Redox Biology, 6: 135-156. (Year: 2015).
Qu et al., Differentiation of human induced pluripotent stem cells to mammary-like organoids, Stem Cell Reports, 2017, 8(2):205-215.
Rey, et al., Chapter 7, Sexual Differentiation, 2016 [online]. [Retrieved on Sep. 19, 2019]. Retrieved from the internet <URL:https://www.endotext.org/wp-content/uploads/pdfs/sexual-differentiation.pdf>, 89 pages.
Ryan et al., Isogenic Human iPSC Parkinson's Model Shows Nitrosative Stress-Induced Dysfunction in MEF2-PGCI [alpha] Trans, Cell, Elsevier, 2013, vol. 155, No. 6, pp. 1351-1364.
Sanchez-Danes et al., Disease-specific phenotypes in dopamine neurons from human iPS-based models of genetic and sporadic Parkinson's disease, EMBO Molecular Medicine, 2015, vol. 4, No. 5, pp. 380-395.
Simeone et al., The Otx Family, Pattern Formation and Development Mechanisms, 2002, vol. 12, pp. 409-415.
Sun et al., Role of Bone Morphogenetic Protein-2 in Osteogenic Differentiation of MesenChymal Stem Cells, Molecular Medicine Reports, 2015, vol. 12, pp. 4230-4237.
Vogel et al., Co-culture of human induced pluripotent stem cells 9iPSCs) with human fallopian tube epithelium (FTE) induces Pax8 and CK7 expression: Initial steps in modeling fallopian tube epithelium to study serous carcinogenesis; Gynecologic Oncology, 2015 137(1):206.
Zhang et al., Regulation and Patterning of Cell Differentiation and Pluripotency, Thesis, Columbia University, pp. 1-177, 2011.
Zhang et al., FGF Ligands of the Postnatal Mammary Stroma Regulate Distinct Aspects of Epithelial Morphogenesis, Stem Cells and Regeneration, 2014, vol. 141, pp. 3352-3362.

(56) References Cited

OTHER PUBLICATIONS

Zhou et al., Rapid and efficient generation of transgene-free iPSC from a small volume of cryopreserved blood, Stem Cell Reviews and Reports 11: 652-665. (Year: 2015).
International Search Report and Written Opinion of PCT Application No. PCT/US2017/013250, Dated Mar. 31, 2017, 12 Pages.
International Search Report and Written Opinion of PCT Application No. PCT/US2016/057724, Dated Jan. 9, 2017, 17 Pages.
International Search Report and Written Opinion of PCT/US2017/016098, Dated Jun. 22, 2017, 14 Pages.
International Search Report and Written Opinion of PCT/US2017/016079, Dated Jul. 25, 2017, 26 Pages.
International Search Report and Written Opinion of PCT/US2017/049193, Dated Nov. 6, 2017, 9 Pages.
International Search Report and Written Opinion of PCT/US2017/049115, Dated Nov. 28, 2017, 11 Pages.
International Search Report and Written Opinion of PCT/US2018/022511, Dated Jul. 26, 2018, 11 Pages.
International Search Report and Written Opinion of PCT/US2018/033498, Dated Aug. 9, 2018, 9 Pages.
International Search Report and Written Opinion for PCT/US2018/022455 dated Aug. 23, 2018, 13 pages.
International Preliminary Report on Patentability for PCT/US2016/057724 dated Apr. 24, 2018, 15 pages.
International Preliminary Report on Patentability for PCT/US2017/013250 dated Jul. 17, 2018, 7 pages.
International Preliminary Report on Patentability for PCT/US2017/016098 dated Aug. 7, 2018, 10 pages.
International Preliminary Report on Patentability for PCT/US2017/016079 dated Aug. 7, 2018, 21 pages.
International Preliminary Report on Patentability for PCT/US2018/022511, dated Sep. 17, 2019, 8 pages.
International Preliminary Report on Patentability for PCT/US2018/022455 dated Aug. 23, 2018, 9 pages.
International Preliminary Report on Patentability for PCT/US2018/033498 dated Nov. 19, 2019, 8 pages.
International Preliminary Report on Patentability for PCT/US2017/049193 dated Mar. 5, 2019, 8 pages.
International Preliminary Report on Patentability for PCT/US2017/049115 dated Mar. 5, 2019, 8 pages.
International Search Report and Written Opinion of PCT/US2019/023749, Dated Jun. 25, 2019, 12 Pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
GB1811716.8 Examination Report dated Feb. 12, 2020, 6 pages.
GB 1903007.1 Search Report dated Apr. 1, 2019, 8 pages.
SG 11201803143Y Search Report dated Jul. 15, 2019, 3 pages.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brown et al., Recreating Blood-Brain Barrier Physiology and Structure on Chip: A Novel Neurovascular Microfluidic Bioreactor, 2015, Biomicrofluidics, vol. 9(5).
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Date et al., Mini-Gut Organoids: Reconstruction of the Stem Cell Niche, Annu. Rev. Cell Dev. Biol., 2015, vol. 31, pp. 269-289.
Dhumpa et al., Temporal Gradients in Microfluidic Systems to Probe Cellular Dynamics: A Review, Anal. Chim. Acta, 2012, vol. 743, pp. 9-18.
Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.
Huh et al., Microfabrication of Human Organs-on-Chips, Nature Protocols, 2013, vol. 8(11), pp. 2135-2157.
Hynds et al., Concise Review: The Relevance of Human Stem Cell-Derived Organoid Models for Epithelial Transitional Medicine, Stem Cells, 2013, vol. 1 31, pp. 417-422.

(56) References Cited

OTHER PUBLICATIONS

Jang et al., JAK-STAT Pathway and Myogenic Differentiation, JAKSTAT, 2013, vol. 2(2), pp. e23282-1 to e-23282-6.
Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.
Kilic et al., Brain-on-a-Chip Model Enables Analysis of Human Neuronal Differentiation and Chemotaxis, 2016, Lab on a Chip, vol. 16(21), pp. 4152-4162.
Kim et al., Human Gut-on-a-Chip Inhabited by a Microbial Flora that Experiences Intestinal Peristalsis-Like Motions and Flow, Lab on a Chip, 2012, vol. 12(12). pp. 2165.
Kim et al., Gut-on-a-Chip Microenvironmental Induces Human Intestinal Cells to Undergo Villus Differentiation, Integrative Biology, 2013, vol. 5(9), p. 1130-1140.
Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.
Kirkby et al., A Role for Correlated Spontaneous Activity in the Assembly of Neural Circuits, 2013, Neuron, vol. 80(5), 27 Pages.
Lenner, J., Fat Cells More Easily Programmed into iPS Cells, 2009, pp. 1-2.
Lin et al., Neural Stem Cell Differentiation in a Cell-Collagen-Bioreactor Culture System, 2004, Developmental Brain Research, vol. 153, pp. 163-173.
Lippmann, et al., Human Blood-Brain Barrier Endothelial Cells Derived from Pluripotent Stem Cells, 2012, Nature Biotechnology, vol. 30(8), pp. 783-791.
Lippmann et al., A Retinoic Acid-Enhanced, Multicellular Human Blood-Brain Barrier Model Derived from Stem Cell Sources, Scientific Reports, vol. 4(1), 2014, pp. 1-10.
Lippmann et al., Chemically Defined Differentiation of Human Pluripotent Stem Cells to Hindbrain and Spinal Cord Neural Stem Cells with Defined Regional Identifies, 2015, Protocol Exchange.
Martin et al., Laparoscopic Colorectal Resection in the Obese Patient, 2011, Clinics in Colon and Rectal Surgery, vol. 24(4), pp. 263-273.
Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.
Medical Dictionary—MYOTUBE, Downloaded on Jul. 8, 2018, https://medical-dictionary.thefreedictionary.com/myotube, p. 1.
Murphy et al., Scaffolds for 3D in vitro Culture of Neural Lineage Cells, Acta Biomaterialia, 2017, vol. 54, pp. 1-20.
Nicoleau et al., Embryonic Stem Cells Neural Differentiation Qualifies the Role of Wnt/[beta]-Catenin Signals in Human Telecephalic Specification and Regionalization: Human ESC Telencephalic Differentiation, Stem Cells, 2013, vol. 31(9), pp. 1763-1774.
Niego et al., Improved Method for the Preparation of a Human Cell-based, Contact Model of the Blood-Brain Barrier, 2013, J. Vis. Exp., vol. 81(e50934), pp. 1-9.
Nostro et al., Efficient Generation of NKX6-1+ Pancreatic Progenitors from Multiple Human Pluripotent Stem Cell Lines, Stem Cell Reports, 2015 4(4), pp. 591-604.
Ochetta et al., High-Throughput Microfluidic Platform for 3D Cultures of Mesenchymal Stem Cells, Towards Engineering Developmental Processes, Scientific Reports, 2015, vol. 5, Article No. 10288, pp. 1-12.
Okita et al., A More Efficient Method to Generate Integration-Free Human iPS Cells, 2011, Nature Methods, vol. 8(5), pp. 409-412.
Ong et al., A Gel-Free 3D Microfluidic Cell Culture System, Biomaterials, 2008, vol. 29, pp. 3237-3244.
Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.
Polini et al., Organs-on-a-Chip: A New Tool for Drug Discovery, Expert Opinion on Drug Discovery, 2014, vol. 9(4), pp. 335-352.
Prabhakarpandian et al., SyM-BBB: A Microfluidic Blood Brain Barrier Model, Lab on a Chip, 2013, vol. 13(6), p. 1093.
Qian et al., A Simple and Efficient System for Regulating Gene Expression in Human Pluripotent Stem Cells and Derivatives, Stem Cells, 2014, vol. 32(5), pp. 1230-1238.
Rajesh et al., Human Lymphoblastoid B-Cell Lines Reprogrammed to EBV-FREE Induced Pluripotent Stem Cells, 2011, Blood, vol. 118(7), pp. 1797-1800.
Rhee et al., Patterned Cell Culture Inside Microfluidic Devices, Lab Chip, 2005, vol. 5(1), pp. 102-107.
Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.
Rosenberg et al., Calcium Signaling in Neuronal Development, 2011, Cold Spring Harb Perspect Biol., vol. 3(a004259), 13 Pages.
Sareen et al., Human Neural Progenitor Cells Generated from Induced Pluripotent Stem Cells can Survive, Migrate, and Integrate in the Rodent Spinal Cord, Journal of Comparative Neuroloy, 2014, vol. 522(12), pp. 2707-2728.
Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.
Shimojo et al., Rapid, Efficient and Simple Motor Neuron Differentiation from Human Pluripotent Stem Cells, Molecular Brain, 2015, vol. 8(1), pp. 1-15.
Shimuzu et al., Microfluidic Devices for Construction of Contractile Skeletal Muscle Microtissues, J. Biosci. Bioeng., 2015, vol. 119, pp. 212-216.
Soria-Valles et al., NF-κB Activation Impairs Somatic Cell Reprogramming in Ageing, 2015, Nat. Cell Biol., vol. 17(8), pp. 1004-1013.
Stepniewski et al., Induced Pluripotent Stem Cells as a Model for Diabetes Investigation, Scientific Reports, 2015, 5:8597, 14 pages.
Telias et al., Electrical Maturation of Neurons Derived from Human Embryonic Stem Cells, F1000 Research, 2014, vol. 3(196), p. 1-12.
Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.
Uzel et al., New Microfluidic Chip Replicates Muscle-Nerve Connection, 2016, Science Daily, pp. 1-4.
Vatine et al., Human iPSC-Derived Blood-Brain Barrier Chips Enable Disease Modeling and Personalized Medicine Applications, Cell Stem Cell, 2019, vol. 24(6), pp. 995-1005.
Vatine et al., Human iPSC-Derived Blood-Brain Barrier Chips Enable Disease Modeling and Personalized Medicine Applications, Cell Stem Cell, 2019, vol. 24, Supplemental Figures, p. 1-10.
Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.
Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.
Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.
Wehkamp et al., Reduced Paneth Cell [alpha]-Defensins in Ileal Crohn's Disease, PNAS, 2005, vol. 102, pp. 18129-18134.
Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.
Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.
Zilio et al., Universal Hydrophilic Coating of Thermoplastic Polymers Currently Used in Microfluidics, 2014, Biomed. Microdevices, vol. 16(1), pp. 107-114.
Fridley et al., Hydrodynamic modulation of pluripotent stem cells, Stem cell research & therapy,2012, vol. 45.

(56) References Cited

OTHER PUBLICATIONS

Zhang et al., Patient-specific 3D microfluidic tissue model for multiple myeloma, Tissue Engineering Part C: Methods, 2014, pp. 663-670.
Jenke et al., DNA Methylation Analysis in the Intestinal Epithelium—Effect of Cell Separation on Gene Expression an Methylation Profile, PLOS One, 2013, vol. 8(2), pp. 1-8.
Brittan et al., The gastrointestial stem cell, Cell Prolif., 2004, vol. 37, pp. 35-53.
Yamamoto et al., The Stabilization Effect of Mesenchymal Stem Cells on the Formation of Microvascular Networks in a Microfluidic Device, Journal of Biomechanical Science and Engineering, 2013, vol. 8(2).
Danmark et al., Development of a novel microfluidic device for long-term in situ monitoring of live cells in 3-dimensional matrices, Biomed Microdevices, 2012, pp. 885-893.
Yu et al., A Microfluidic-Based Multi-Shear Device for Investigating the Effects of Low Fluid-Induced Stresses on Osteoblasts, PLOS One, 2014, vol. 9(2), pp. 1-7.
GB 1903007.1 Search Report dated Jun. 24, 2020, 3 pages.
Extended European Search Report for EP 18802136.4 dated Jan. 22, 2021, 12 pages.
Kuratnik et al., Intestinal organoids at tissue surrogates for toxicological and pharmacological studies, biochemical Pharmacology, Apr. 25, 2013, vol. 85:12, pp. 1721-1726.
Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.
Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.
Lee et al. Microfluidic 3D bone tissue model for high-throughput evaluation of would healing and infection-preventing biomaterials, Biomaterials 33.4 2012 999-1006.
Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.
Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.
Written Opinion 11201901628X dated Mar. 10, 2021, 9 pages.
Notice of Reasons for Rejection for JP 2018-540028 dated Mar. 1, 2021.
EP 19771249.0 Partial Supplemental European Search Report dated Nov. 8, 2011, 15 pages.
EP 18802136.4 Examination Report dated Oct. 14, 2021, 8 pages.
Abbott et al., Structure and function of the blood-brain barrier, Neurobiology of Desease, 2010 27:13-25.
Abbott et al., Structure and function of the blood-brain barrier, Pharm Tox BBB: 1-3, Feb. 2010, Conf. Abstract.
Demers et al., Development-on-Chip: in vitro Neutral Tube Patterning with a Microfluidic Device, Development, 2016, vol. 143(11), pp. 1884-1892.
Kauffman et al., Alternative functional in vitro models of human intestinal epithelia, frontiers in Pharmacology, Jul. 2013, vol. 4, Article 79, 18 pages.
Kelamangalath et al. κ-Opioid receptor inhibition of calcium oscillations in spinal cord neurons,, Molecular Pharmacology, 2011, 79:1061-1071.
Kwasny et al., Static biofilm cultures of gram-positive pathogens grown in a microtiter format used for anti-biofilm drug discovery, Current Protocols in Pharmacology, 2010, 13A.8.1-13A.8.23.
Loo et al., An Arduous Journey from Human Pluripotent Stem Cells to Functional Pancreatic Beta Cells, Diabetes Obes Metab., 2018, vol. 20(3), pp. 3-13.
McGaugh et al., Efficient Differentiation of Pluripotent Stem Cells to NKX6-1 + Pancreating Progenitors, Journal of Visualized Experiments, 2017, vol. 121, pp. 1-5.
Naik et al., In vitro blood-brain models: Current and perspective technologies, J. Phar Sci., 2012, 1014(4):1337-1354.
Perry et al., The Neuromuscular junction: Structure and function, downloaded from the internet (Neuromuscular junction: Parts, structure and steps/Kenhub>, pp. 1-6, downloaded Feb. 25, 2021.
Polydimethylsiloxane-Wikipedia, dowloaded on Feb. 24, 2021 <Silicon dioxide—Wikipedia>, pp. 1-11.
Ryan et al., Progranulin is expressed within motor neurons and promotes neuronal cell survival, BMC Neuroscience, 2009, 10:130, pp. 1-22.
Sances et al., Modeling ALS with Motor Neurons Derived from Human Induced Pluripotent Stem Cells, Nature Neuroscience , 2016, vol. 19, pp. 542-553.
Santaguida et al., Side by Side Comparison Between Dynamic Versus Static Models of Blood-Brain-Barrier in vitro: A Permeability Study, Brain Research, 2006, vol. 1109(1), pp. 1-13.
Schiesser et al., Derivation of Insulin-Producing Beta-Cells from Human Pluripotent Stem Cells, The Review of Diabetic Studies, 2014, vol. 11(1), pp. 6-18.
Schwartz et al., Allan-Herndon-Dudley Syndrome and the Monocarboxylate Transporter 8 (MCT8) Gene, 2005, AJHG, vol. 77(1), pp. 41-53.
Silicon dioxide-Wikipedia, downloaded on Feb. 24, 2021 <silicon dioxide—Wikipedia> pp. 1-20.
Southam et al., Microfluidic primary culture model of the lower motor neuron-neuromuscular junction circuit, J Neurosc Meth 2013, 218:164-169.
Southam et al., A Novel in vitro Primary Culture Model of the Lower Motor Neuron—Nueromuscular Junction Circuit, Microfludic and Compartmentalized Platforms for Neurobiological Research, Humana Press, 2015, pp. 181-193, abstract only.
Uzei et al., Microfluidic Device for the Formation of Optically Excitable, Three-Dimensional, Compartmentalized Motor Units, Science Advances, 2016, pp. e1501429.
Wang et al., Microfluidics: A new cosset for neurobiology, Lab Chip, 2009, 9:644-652.
Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.
Yang et al., From the vascular microenvironment to neurogenesis, Brain Res Bull. Jan. 15, 2011; 84(1):1-7.
Recchia et al., a-Synuclein and Parkinson's disease, The FASEB Journal, 2004, 18:617-626.
Yuan et al., Overexpression of a-Synuclein down-regulates BDNF Expression, Cell and Molecular Neurobiology, 2010, 30:939-946.
Oceguera-Yanez et al., Engineering the AAVS1 locus for consistent and scalable transgene expression in human IPSCs and their differentiated derivatives, Methods, 2016, 1:43-55.
ISR and WO for PCT/US2021/051492 mailed Dec. 27, 2021, 11 pages.
Lamas et al., Neurotrophic Requirements of Human Motor Neurons Defined Using Amplified and Purified Stem Cell-Derived Cultures, PLosOne, Oct. 22, 2014, vol. 9, No. 10, pp. 1-13.
Li et al., An integrated multi-omic analysis of IPSC-derived motor neurons from C9ORF72 ALS patients, iScience, Oct. 12, 2021, vol. 24, No. 11, pp. 1-33.
EESR for EP 21873328.5 dated Sep. 5, 2024, 9 pages.
Hoveizi et al., Differential effect of Activin A and WNT3a on definitive endoderm differentiation on electrospun nanofibrous PCL scaffold, Cell Biology International, 2015, 9999, pp. 1-9.
Kosar et al., A nanofabricated planar aperture as a mimic of the nerve-muscle contact during synaptogenesis, Lab on a Chip, 2016, 6:632-638.
Guo et al., Neuromuscular junction formation between human stem cell-derived motoneurons and human skeletal muscle in a defined system, Biomaterials, 2011 32:9602-9611.
Adams et al., Development of flexible arrays for in vivo neuronal recording and stimulation, Nuclear Instruments & Methods in Physics Research, 2005, 546:154-159.

(56) References Cited

OTHER PUBLICATIONS

Baloh et al., "Transplantation of human neural progenitor cells secreting GDNF into the spinal cord of patients with ALS: a phase 1/2a trial." Nature medicine 28.9 (2022): 1813-1822.
Faravelli et al., "Motor neuron derivation from human embryonic and induced pluripotent stem cells: experimental approaches and clinical perspectives." Stem cell research & therapy 5 (2014): 87.
Klein et al., "GDNF delivery using human neural progenitor cells in a rat model of ALS." Human gene therapy 16.4 (2005): 509-521.
Extended European Search Report in European Patent Application No. 20878850, mailed Dec. 8, 2023 (12 pages).
EPO Communication Article in European Patent application No. 18802136, mailed Mar. 17, 2023 (10 pages).
Examination Report in Australian Patent Application No. 2017321489, Mailed Mar. 7, 2023 (4 pages).
Sareen et al., Human induced pluripotent stem cells are a novel source of neural progenitor cells (iNPCs) that migrate and integrate in the rodent spinal cord: Human neural progenitor cells, 2014. Journal of Comparative Neurology, vol. 522, No. 12, pp. 2707-2728.
Office Action in Canadian Patent Application No. 3,034,614, mailed Jan. 28, 2025 (3 pages).
Exam Search Report and Written Opinion in Singaporian Patent Application No. 11201901621V, mailed May 12, 2020 (12 pages).
Achyuta A.K.H. et al., A modular approach to create a neurovascular uniton-a-chip. Lab Chip, Sep. 26, 2012, vol. 13, No. 4, pp. 542-553.
EPO Communication in European Patent Application No. 19796470, mailed Jan. 16, 2024 (10 pages).
Klepac et al. "An update on the management of young-onset Parkinson's disease." Degenerative neurological and neuromuscular disease (2013): 53.
Notice of Reasons for Rejection in Japanese Patent Application No. 2020-560894, mailed Apr. 4, 2023 (6 pages).
Wu et al., "Nuclear accumulation of histone deacetylase 4 (HDAC4) exerts neurotoxicity in models of Parkinson's disease." Molecular neurobiology 54 (2017): 6970-6983.
Offica Action in Chinese Patent Application No. 202080074079, mailed Aug. 11, 2023 (11 pages).
Laperle et al., "Human iPSC-derived neural progenitor cells secreting GDNF provide protection in rodent models of ALS and retinal degeneration." Stem cell reports 18.8 (2023): 1629-1642.
Akhtar et al., "Inducible expression of GDNF in transplanted iPSC-derived neural progenitor cells." Stem Cell Reports 10.6 (2018): 1696-1704.
Romero-Ramos et al., Neuronal differentiation of stem cells isolated from adult muscle, Journal of Neuroscience Research, 2002, 69:894-907.
PSA (Aniti-anti) Antibiotic-Antimycotic Solution (100X)-cell culture-TOKU-2 pages downloaded from internet on Jun. 2, 2025, 2025.
Elis et al., Human IPSC-derived myocardium-on-chip with capillary-like flow for personalized mediine, Biomicrofluidics 11, 024105, 2017.
Cardiac cells, Science Direct <https://www.sciencedirect.com/topics/engineering/cardiac-cell>; 2025.
CA Exam Report for CA 3158428 dated Oct. 8, 2025, 5 pages.
Zhou et al., "The positional identity of iPSC-derived neural progenitor cells along the anterior-posterior axis is controlled in a dosage-dependent manner by bFGF and EGF", Differentiation, 92(4), pp. 183-194, Oct. 2016.
Xu et al., "Effect of leukocyte inhibitory factor on neuron differentiation from human induced pluripotent stem cell-derived neural precursor cells", International Journal of Molecular Medicine, 41(4), pp. 2037-2049, Apr. 2018.
McCaughey-Chapman et al., "Human Cortical Neuron Generation Using Cell Reprogramming: A Review of Recent Advances", Stem Cells and Development, 27(24), pp. 1674-1692, Dec. 2018.
Roberts et al., Fluorescent gene tagging of transcriptionally silent genes in hiPSCs, Stem Cell Reports, 2019, 12:1145-1158.
Osaki et al., Microphysiological 3D model of amyotrophic lateral sclerosis (ALS) from human iPS-derived muscle cells and optogenetic motor neurons, Science Advances, 4 eeat5847, 2018.
Osaki et al., Engineered 3D vascular and neuronal networks in a microfluidic platform, Scientific Reports, 8, 5168, 2018.
Shinde et al., A complex network of microRNAs expressed in brain and genes associated with amyotrophic lateral sclerosis, International Journal of Genomics, 383024, 2014.

* cited by examiner

FIG. 1

| Patient | KB | BH | CR |
|---|---|---|---|
| Age | 32 | 37 | 39 |
| Gender | F | M | M |
| PD Duration | 1.5 | 5 | 4 |
| Motor subtpe | Mixed | Mixed | Tremor-predominant |
| Hoen & Yahr | 1 | 1 | 1 |
| Reported Family history of PD/Tremor | None | None | None |
| PD SNP Familial Mutation | Negative | Negative | Negative |
| DaTscan Results | Positive | Positive | Positive |
| IPSC Line | 190iPD | 194iPD | 200iPD |

| Patient | CTRL 1 | CTRL 2 | CTRL 3 |
|---|---|---|---|
| Sex | M | M | M |
| Age at Collection | 51 | 37 | 6 |
| Sample Type | Blood (T Fraction) | Blood (NT Fraction) | Fibroblast |
| iPSC Line | 02iCTR | WP3iCTR | 00iCTR |

C-RTI 32 DAT
I-ioflupane DAT
Tc-TRODAT DAT
C-DTB2 VWAT2
F-dopa DDC
Healthy
PD

C-RTI 32 DAT
I-ioflupane DAT
Tc-TRODAT DAT
C-DTB2 VWAT2
F-dopa DDC
Healthy
PD

C-RTI 32 DAT
I-ioflupane DAT
Tc-TRODAT DAT
C-DTB2 VWAT2
F-dopa DDC
Healthy
PD a
Days
0
3
7
11
14
20
25
30
LDN/SB
LDN
Shh/PMN/FGF8
CHIR
ATRA
Maturation Medium
b
c
% TH+
40
30
20
10
0
ns
*
02iCTR
WP3iCTR
00iCTR
190iPD
194iPD
200iPD d
Total Dopamine (nM)
10
8
6
4
2
0

*
02iCTR
WP3iCTR
00iCTR
190iPD
194iPD
200iPD
e
nM Dopamine per TH+ Cell
0.003
0.002
0.001
0.000
ns
CTRL
PD
f
β-Act
α-Synuclein
02iCTR
WP3iCTR
00iCTR
190iPD
194iPD
200iPD
g
Rel Intensity to Ave CTRL
4
3
2
1
0
*
CTRL
PD
h
Fold Change rel to CTRL
2.0
1.5
1.0
0.5
0.0
ns
CTRL
PD

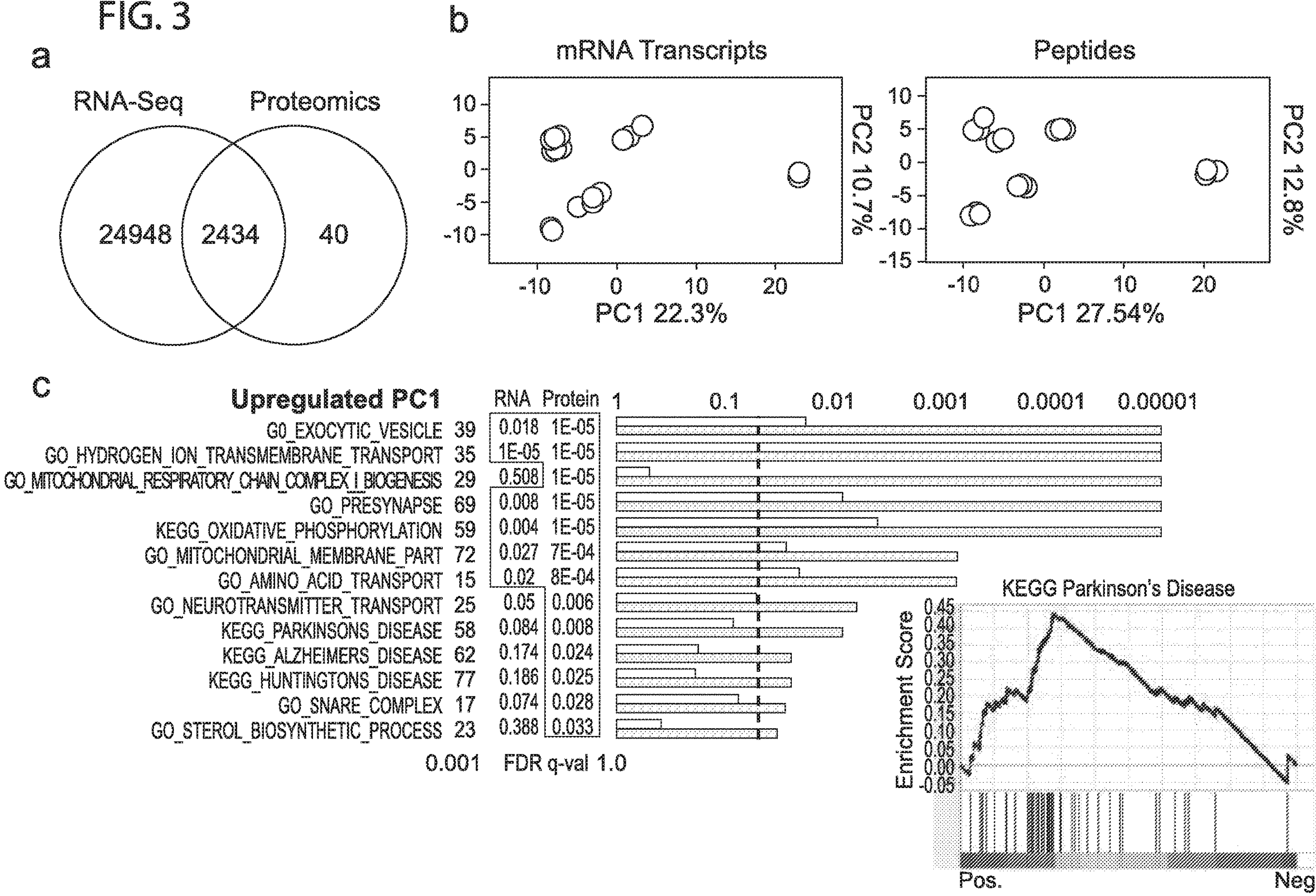
FIG. 3
a
RNA-Seq
Proteomics
24948
2434
40
b
mRNA Transcripts
Peptides
PC2 10.7%
PC2 12.8%
PC1 22.3%
PC1 27.54%
c
Upregulated PC1
RNA Protein
G0_EXOCYTIC_VESICLE 39 0.018 1E-05
GO_HYDROGEN_ION_TRANSMEMBRANE_TRANSPORT 35 1E-05 1E-05
GO_MITOCHONDRIAL_RESPIRATORY_CHAIN_COMPLEX_I_BIOGENESIS 29 0.508 1E-05
GO_PRESYNAPSE 69 0.008 1E-05
KEGG_OXIDATIVE_PHOSPHORYLATION 59 0.004 1E-05
GO_MITOCHONDRIAL_MEMBRANE_PART 72 0.027 7E-04
GO_AMINO_ACID_TRANSPORT 15 0.02 8E-04
GO_NEUROTRANSMITTER_TRANSPORT 25 0.05 0.006
KEGG_PARKINSONS_DISEASE 58 0.084 0.008
KEGG_ALZHEIMERS_DISEASE 62 0.174 0.024
KEGG_HUNTINGTONS_DISEASE 77 0.186 0.025
GO_SNARE_COMPLEX 17 0.074 0.028
GO_STEROL_BIOSYNTHETIC_PROCESS 23 0.388 0.033
0.001 FDR q-val 1.0
1
0.1
0.01
0.001
0.0001
0.00001
KEGG Parkinson's Disease
Enrichment Score
Pos.
Neg.

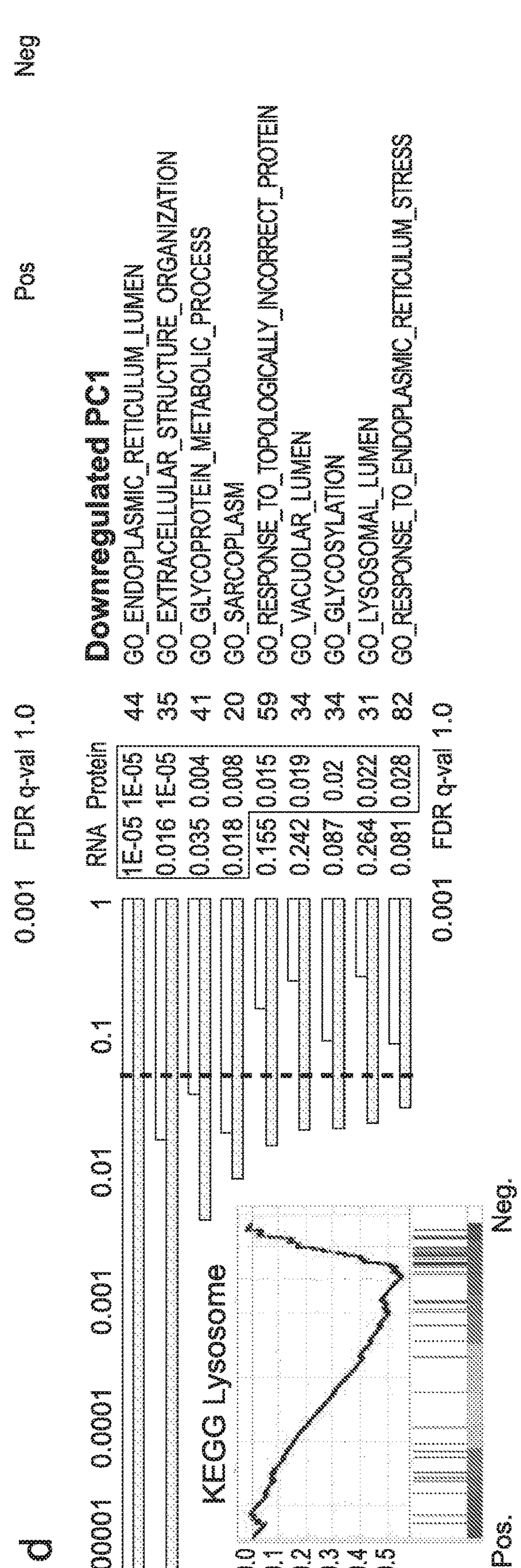
FIG. 3
d
0.00001
0.0001
0.001
0.01
0.1
1
0.001 FDR q-val 1.0
Pos
Neg
RNA Protein
Downregulated PC1
1E-05 1E-05 44 GO_ENDOPLASMIC_RETICULUM_LUMEN
0.016 1E-05 35 GO_EXTRACELLULAR_STRUCTURE_ORGANIZATION
0.035 0.004 41 GO_GLYCOPROTEIN_METABOLIC_PROCESS
0.018 0.008 20 GO_SARCOPLASM
0.155 0.015 59 GO_RESPONSE_TO_TOPOLOGICALLY_INCORRECT_PROTEIN
0.242 0.019 34 GO_VACUOLAR_LUMEN
0.087 0.02 34 GO_GLYCOSYLATION
0.264 0.022 31 GO_LYSOSOMAL_LUMEN
0.081 0.028 82 GO_RESPONSE_TO_ENDOPLASMIC_RETICULUM_STRESS
0.001 FDR q-val 1.0
KEGG Lysosome
Enrichment Score
0.0
-0.1
-0.2
-0.3
-0.4
-0.5
Pos.
Neg.

a
02iCTR
190iPD
Time post CXC (hrs) 0 12 24 48 0 12 24 48
α-Synuclein
TH
Synaptophysin
b
Fold Change rel to T=0
0 1 2 3
0 20 40 60
Time (hrs) post CXC Addition
02iCTR
190iPD
c
Fold Change rel to T=0
0.0 0.5 1.0 1.5
0 20 40 60
Time (hrs) post CXC Addition
02iCTR
190iPD
d
Fold Change rel to T=0
0.0 0.5 1.0 1.5
0 20 40 60
Time (hrs) post CXC Addition
02iCTR
190iPD FIG. 4
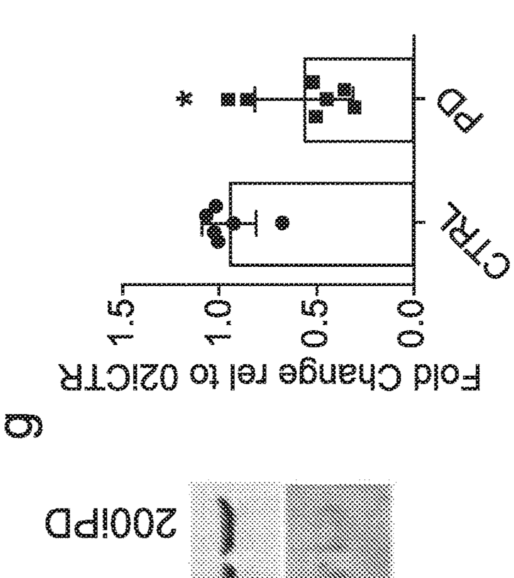
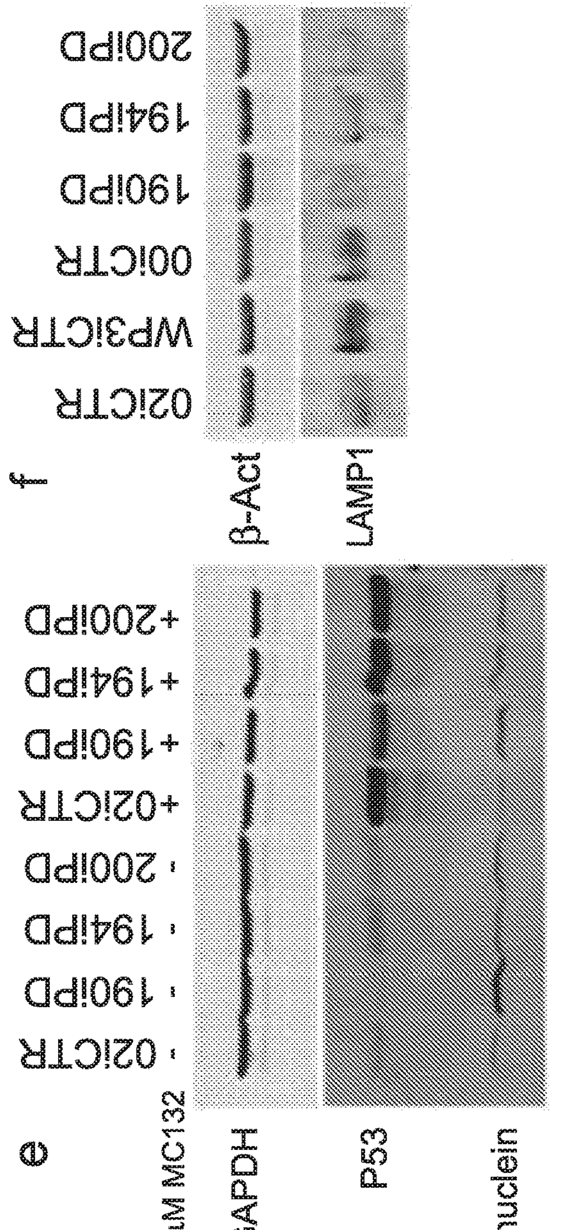
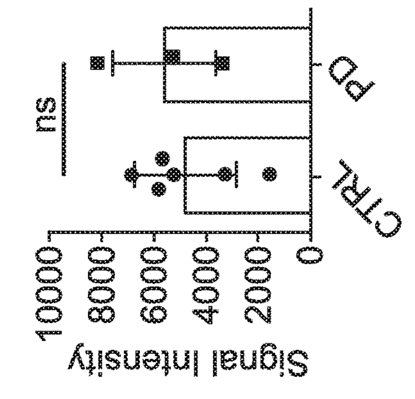

a
02iCTR
190iPD
Untreated
1μM PEP005
5μM SMER-28
25mM Trehalose
Untreated
1μM PEP005
5μM SMER-28
25mM Trehalose
β-Act
α-Synuclein
TH
p-PKCα
α-Synuclein
Signal rel to Untreated
1.5
1.0
0.5
0.0
Untreated
PEP
SMER
TRE
Drug Treatment
02iCTR
190iPD
TH
Signal rel to Untreated
1.5
1.0
0.5
0.0
Untreated
PEP
SMER
TRE
Drug Treatment
b
02iCTR
WP3iCTR
00iCTR
190iPD
194iPD
200iPD
β-Act
p-PKCα
Fold Change rel to 02iCTR
3
2
1
0
*
CTRL
PD c
02iCTR
190iPD
194iPD
200iPD
1µM PEP005 - + - + - + - +
β-Act
p-PKCα
LAMP1
LC3 MI
α-Synuclein
d
02iCTR
190iPD
Time post PEP 0 2 4 8 24
0 2 4 8 24
β-Act
p-PKCα
α-Synuclein
CC3
02iCTR
190iPD
p-PKCα
α-Synuclein
CC3
p-PKCα
α-Synuclein
CC3
Fold Change rel to T=0
Fold Change rel to T=0
Time (hrs) post 1uM PEP
Time (hrs) post 1uM PEP
TH
02iCTR
Fold Change rel to T=0
Time (hrs) post 1uM PEP

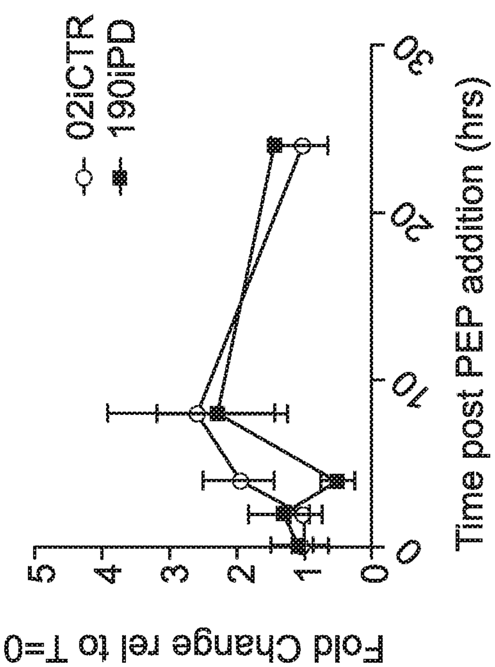
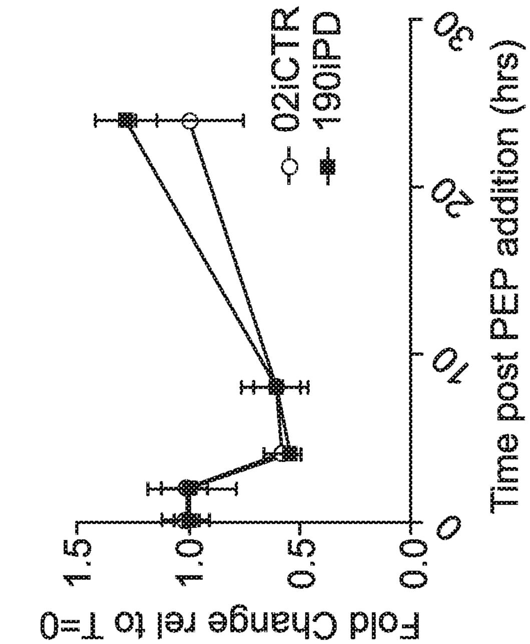
FIG. 5
e

| D14 | D15 | D16 | D17 | D18 | D19 | D20 | D21 | D22 | D23 | D24 | D25 |
|---|---|---|---|---|---|---|---|---|---|---|---|
| Accutase Split*, replate 100k/cm^2 onto matrigel or stage 4 astrocytes** | | | | | | | | | | | |
| Maturation Media | | | | | | | | | | | |
| seed Stage 3 Astrocytes 7 days prior | | | | | | | | | | | |

DIAGNOSTIC AND DRUG SCREENING FOR MOLECULAR SIGNATURES OF EARLY ONSET SPORADIC PARKINSON'S DISEASE

CROSS-REFERENCE TO RELATED APPLICATIONS

This application is a National Phase of International Application No. PCT/US2019/026195, filed Apr. 5, 2019, which designated the U.S. and that International Application was published under PCT Article 21(2) in English, which claims the benefit under 35 U.S.C. § 119(e) to U.S. Provisional Application Ser. No. Ser. No. 62/664,888 filed Apr. 30, 2018; U.S. Provisional Application Ser. No. 62/664,827 filed Apr. 30, 2018; U.S. Provisional Application Ser. No. 62/664,942 filed May 1, 2018; U.S. Provisional Application Ser. No. 62/755,365 filed Nov. 2, 2018; and U.S. Provisional Application Ser. No. 62/816,795 filed Mar. 11, 2019, the contents of which are incorporated herein by reference in their entirety.

STATEMENT REGARDING FEDERALLY-SPONSORED RESEARCH OR DEVELOPMENT

This invention was made with government support under NS105703 awarded by the National Institutes of Health. The government has certain rights in the invention.

FIELD OF THE INVENTION

Described herein are methods and compositions related to production of midbrain neurons, including those related to Parkinson's Disease.

BACKGROUND

Parkinson's Disease (PD) is the second most commonly diagnosed neurodegenerative disorder and represents a substantial economic burden among current aging populations. The classically associated pathology in PD is characterized by the progressive loss of dopaminergic neurons (DaNs) in the substantia nigra pars compacta and the presence of cytoplasmic inclusions known as Lewy bodies and Lewy neurites. These inclusions are composed mainly of the protein α-synuclein. Mutations or triplication of the gene encoding α-synuclein (SNCA) are causal in these specific familial PD cases. In its native state, α-synuclein is found in the presynaptic terminal of neurons throughout the human brain and functions in vesicle trafficking, neurotransmitter release and reuptake.

While many genes and proteins, such as α-synuclein, have been linked to PD, the inability to extract live neurons from patients and the lack of effective PD models leaves unanswered questions regarding the initiation and progression of the disease. Reprogramming patient-derived cells into iPSCs enables the observation of disease progression and pathological phenotypes at a molecular level. Interestingly, previous iPSC studies on the larger non-familial (sporadic) population do not show overt differences when compared those derived from control individuals. Thus, there is a great need in the art for iPSC disease models that represent the complex biological background underpinning Parkinson's disease pathology.

Described herein are compositions and methods for modeling and treating Parkinson's Disease. Importantly, generation of midbrain neurons, floorplate induction in a manner faithfully mirroring development allows for identification of cellular cues leading to neurodegeneration, this includes the complex etiology behind sporadic PD cases that have not yet been fully utilized in iPSC models. Establishing such models, the Inventors herein identified hereto unknown role of α-synuclein and lysosomal degradation dysfunction, as mediated in-party by PKC. Targeting PKC via an agonist improved measurable outcomes, thereby suggesting new therapeutic avenues for Parkinson's Disease.

SUMMARY OF THE INVENTION

Described herein is a method of compound screening, including contacting a quantity of neurons with one or more test compounds, measuring one or more parameters, and selecting one or more test compounds based on the measured one or more parameters, wherein the neurons are differentiated from blood cell-derived induced pluripotent stem cells (iPSCs). In other embodiments, the neurons are midbrain neurons. In other embodiments, the midbrain neurons are dopaminergic neurons. In other embodiments, the one or more parameters comprise PKC activation. In other embodiments, the one or more parameters comprise at least one of TFEB activation and ZKSCAN3 inactivation. In other embodiments, the one or more parameters comprise α-synuclein protein levels. In other embodiments, the one or more parameters comprise at least one of: LAMP1, GCase, tyrosine hydroxylase (TH), and dopaminergic activity. In other embodiments, the one or more parameters comprise at least one of: LAMP, GCase, tyrosine hydroxylase (TH) and dopamine expression levels. In other embodiments, the blood cell-derived iPSCs are made by a method including contacting a quantity of blood cells with one or more oriP/EBNA1 vectors encoding a reprogramming factor, and delivering a quantity of reprogramming factors into the blood cells, culturing the blood cells in a reprogramming media wherein delivering the reprogramming factors, and culturing in a reprogramming media generates blood cell derived iPSCs. In other embodiments, the quantity of blood cells is obtained from a human subject afflicted with a neurodegenerative disease. In other embodiments, the neurodegenerative disease is Parkinson's Disease. In other embodiments, the Parkinson's Disease is early onset Parkinson's Disease. In other embodiments, the neurons are differentiated from blood cell-derived iPSCs by a method including providing a quantity of blood cell-derived induced pluripotent stem cells (iPSCs), culturing the iPSCs in the presence of a transforming growth factor (TGF)-beta inhibitor and an activin receptor-like kinase (ALK) inhibitor, further culturing in the presence of a Smoothened agonist, a RHO Kinase (ROCK) inhibitor and at least two growth factors, additionally culturing in the presence of retinoic acid, and continuing to culture in the presence of at least three additional growth factors. In other embodiments, the transforming growth factor (TGF)-beta inhibitor includes LDN-193189 and the activin receptor-like kinase (ALK) inhibitor includes SB431542, the Smoothened agonist comprises Purmorphamine, the at least two growth factors comprise sonic hedgehog, and fibroblast growth factor 8, the ROCK inhibitor includes CHIR99021, and the at least three additional growth factors comprise brain derived neurotrophic factor, glial derived neurotrophic factor, and TGF-Beta 3.

Also described herein is a method of diagnosis, including assaying one or more biomarkers in a subject suspected of being afflicted with Parkinson's Disease, comparing the expression levels of the one or more biomarkers from the subject to a baseline of the one or more biomarkers derived from healthy subjects without Parkinson's disease, and diagnosing Parkinson's Disease in the subject.

Also described herein is a method of prognosis, including assaying one or more biomarkers in a subject suspected of being afflicted with Parkinson's Disease, comparing the expression levels of the one or more biomarkers from the subject to a baseline of the one or more biomarkers derived from healthy subjects without Parkinson's disease, and prognosing Parkinson's Disease in the subject.

Further described herein is a method of selecting a therapeutic regimen, including assaying one or more biomarkers in a subject suspected of being afflicted with Parkinson's Disease, comparing the expression levels of the one or more biomarkers from the subject to a baseline of the one or more biomarkers derived from healthy subjects without Parkinson's disease, and selecting a therapeutic regimen for the subject.

BRIEF DESCRIPTION OF THE FIGURES

FIG. 1: PD patient data

FIG. 3: Combined detection of overlapping transcripts and proteins from paired RNA-Seq and Proteomics (a). PCA plots of matched transcriptomic and proteomic data (b) GSEA analyses of PCI components upregulated in PD (c) GSEA analysis of PCI components downregulated in PD (d)

Peripheral blood mononuclear cells (PBMCs) were reprogrammed using episomal nucleofection technique involving four plasmids containing Yamanaka reprogramming transcription factors OCT4, KLF, SOX2, MYC, and Lin28. EBNA1 was also included to enhance transfection efficiency. Cells were seeded on gelatin coated tissue culture plates containing a bed of mouse embryonic fibroblasts (MEFs) for 18-26 days. iPSC colony formation occurred in all three lines, multiple clones were collected and expanded over multiple passages. Alkaline Phosphatase (AP) staining (20×) reveals elevated levels in cell membranes of patient lines indicative of undifferentiated tissue. (B) Immunocytochemistry (20×) showing pluripotency gene Oct4 expression. Human specific cell surface antigen marker SSEA4 is also expressed indicating molecular profile consistent with pluripotent cells.

Patient-derived iPSCs can be differentiated to dopaminergic (DA) neurons. Images show 40 day old cultures that express tyrosine hydroxylase (TH) and display typical neuronal morphology. These cells endogenously express α-synuclein, also found in Lewy bodys in patients with Parkinson's disease. Images taken at 20× magnification.

Figure 8:
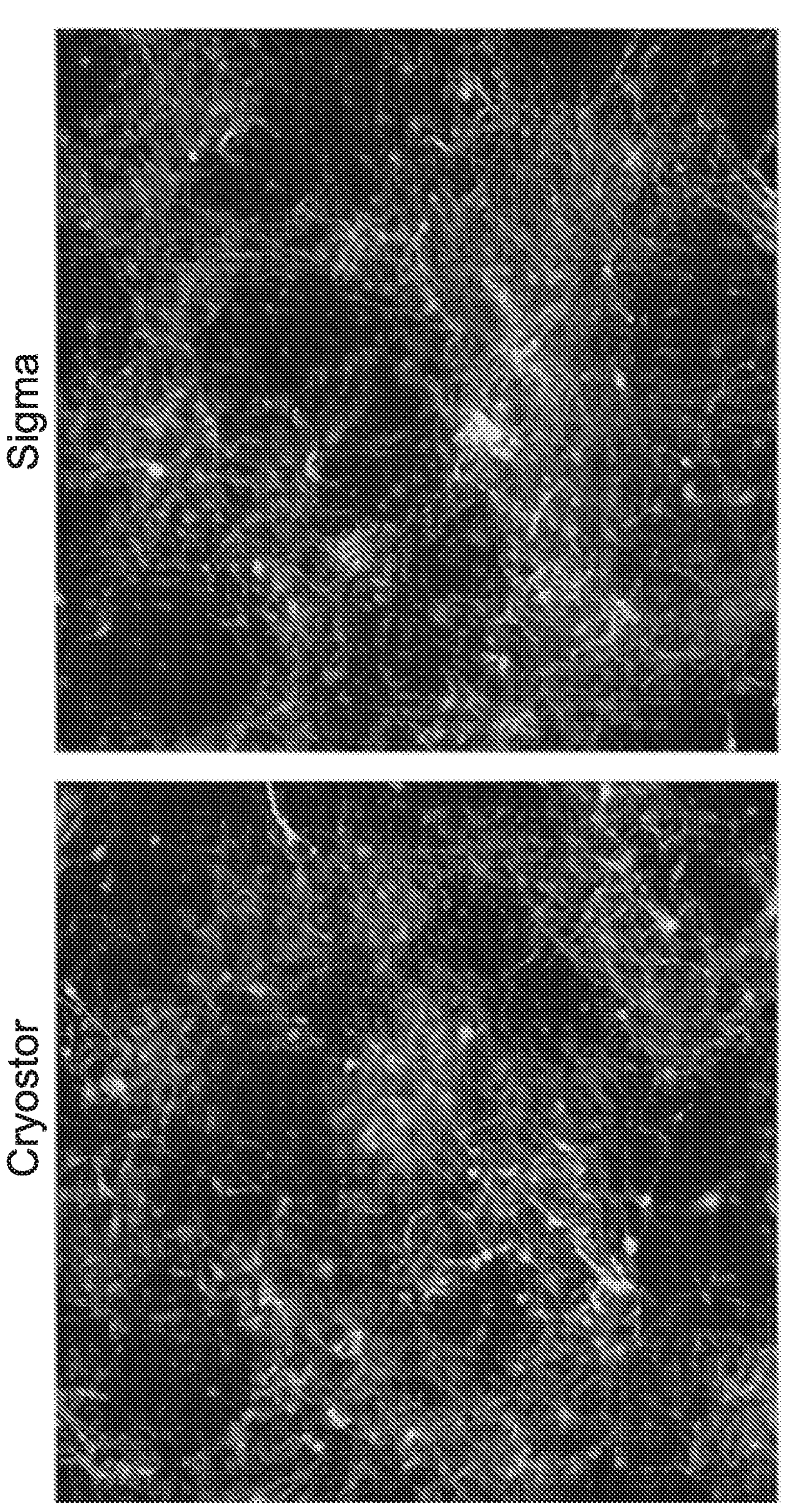

FIG. 8. DANs successfully cryo-banked (02iCTR).

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As described, reprogramming patient-derived cells into iPSCs enables the observation of disease progression and pathological phenotypes at a molecular level. The iPSCs, which are genetically identical to the donor, can be differentiated into DaNs providing a tissue-specific model of Parkinson's Disease in vitro that harbor genetic backgrounds known to relate to clinical presentation in vivo. Recently, an intense effort has been made to elucidate the role of α-synuclein in the origin and progression of PD using similar iPSC modeling techniques. Several studies have employed iPSCs derived from PD patients with monogenic mutations including a triplication of SNCA, as well as mutations in the LRRK2 and GBA1 genes. While DA neurons derived from these iPSC lines display some phenotypic abnormalities and demonstrate accumulation of α-synuclein, familial monogenic mutations are present only in a small minority of PD patients and pathophysiology of these cases are not easily related to the PD population at large. Interestingly, previous iPSC studies on the larger non-familial (sporadic) population do not show overt differences when compared those derived from control individuals.

Here, the Inventors generate iPSC lines from a cohort of early onset sporadic PD (EOSPD) patients. The Inventors hypothesized that these lines represent a promising opportunity to better understand sporadic PD, as early onset sporadic patients could have unknown genetic risk factors that may influence a more aggressive form of the disease. The Inventors show that by comparing differentiated DaNs from either EOSPD patient and non-diseased control lines, aberrant accumulation of α-synuclein protein is indeed specifically reproduced in the PD patient cohort. Molecular and physiological profiling of these tissues including proteomic, whole transcriptomic and enzyme activity assays find dysregulated degradation pathways and implicate a previously unreported upregulation of phosphorylated PKC-α in EOSPD cultures. Finally, by targeting this pathway, the Inventors observe reversal of α-synuclein accumulation after treatment with a small molecule PEP005 both in vitro and in vivo. The iPSC-based model described here provides evidence of the genetic origin of sporadic PD that contributes PD and provides a platform for potential clinical diagnostics and development of new therapeutic targets for EOSPD patients.

Described herein is a method of compound screening, including contacting a quantity of neurons with one or more test compounds, measuring one or more parameters, and selecting one or more test compounds based on the measured one or more parameters, wherein the neurons are differentiated from blood cell-derived induced pluripotent stem cells (iPSCs). In other embodiments, the neurons are midbrain neurons. In other embodiments, the midbrain neurons are dopaminergic neurons. In other embodiments, the one or more parameters comprise PKC activation. In other embodiments, the one or more parameters comprise at least one of TFEB activation and ZKSCAN3 inactivation. In other embodiments, the one or more parameters comprise α-synuclein protein levels. In other embodiments, the one or more parameters comprise at least one of: LAMP1, GCase, tyrosine hydroxylase (TH), and dopaminergic activity. In other embodiments, the one or more parameters comprise at least one of: LAMP, GCase, tyrosine hydroxylase (TH) and dopamine expression levels. In other embodiments, the one or more parameters include permeability of the test compound across a quantity of vascular cells, alterations in electrophysiological properties of the cells, alterations in metabolic profile of the cells, including for example, neurotransmitter production and release. In other embodiments, the iPSCs are made by a method including contacting a quantity of blood cells with one or more oriP/EBNA1 vectors encoding a reprogramming factor and delivering a quantity of reprogramming factors into the blood cells culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived iPSCs.

In other embodiments, the blood cell-derived iPSCs are made by a method including contacting a quantity of blood cells with one or more oriP/EBNA1 vectors encoding a reprogramming factor, and delivering a quantity of reprogramming factors into the blood cells, culturing the blood cells in a reprogramming media wherein delivering the reprogramming factors, and culturing in a reprogramming media generates blood cell derived iPSCs. In other embodiments, the quantity of blood cells is obtained from a human subject afflicted with a neurodegenerative disease. In other embodiments, the neurodegenerative disease is Parkinson's Disease. In other embodiments, the neurodegenerative disease is Parkinson's Disease (PD), including familial, sporadic and early onset PD. In other embodiments, the Parkinson's Disease is early onset Parkinson's Disease. Further information on iPSC reprogramming is found in Barrett, R. et al. Reliable Generation of Induced Pluripotent Stem Cells from Human Lymphoblastoid Cell Lines. *Stem Cells Transl Med.* 2014 December; 3(12):1429-34, which is fully incorporated by reference herein.

In other embodiments, the neurons are differentiated from blood cell-derived iPSCs by a method including providing a quantity of blood cell-derived induced pluripotent stem cells (iPSCs), culturing the iPSCs in the presence of a transforming growth factor (TGF)-beta inhibitor and an activin receptor-like kinase (ALK) inhibitor, further culturing in the presence of a Smoothened agonist, a RHO Kinase (ROCK) inhibitor and at least two growth factors, additionally culturing in the presence of retinoic acid, and continuing to culture in the presence of at least three additional growth factors. In other embodiments, the transforming growth factor (TGF)-beta inhibitor includes LDN-193189 and the activin receptor-like kinase (ALK) inhibitor includes SB431542, the Smoothened agonist comprises Purmorphamine, the at least two growth factors comprise sonic hedgehog, and fibroblast growth factor 8, the ROCK inhibitor includes CHIR99021, and the at least three additional growth factors comprise brain derived neurotrophic factor, glial derived neurotrophic factor, and TGF-Beta 3. In various embodiments, the concentrations of the aforementioned agents are as described in Table 1. In other embodiments, the iPSCS are made by a process including contacting a quantity of blood cells with one or more vectors encoding a reprogramming factor, and delivering a quantity of reprogramming factors into the blood cells, culturing the blood cells in a reprogramming media. In other embodiments, the one or more vectors are oriP/EBNA1 vectors. In other embodiments, culturing iPSCs is for about 3 days. In other embodiments, further culturing is for about 4 days. In other embodiments, additionally culturing is for about 4 days. In other embodiments, continuing to culture is for at least 3 days. In other embodiments, the differentiation schedule, including feeding and media changes is according to Table 1 and FIG. 6. Additional information can be found in U.S. Prov. App. No. 62/653,697 and 62/755,282, U.S. Prov. App. No. 62/653,697, U.S. Prov. App. No. 62/755,282, U.S. Prov. App. No. 62/816,785, U.S. Prov. App. No. 62/664,888, U.S. Prov. App. No. 62/664,827, U.S. Prov. App. No. 62/816,795, U.S. Prov. App. No. 62/664,942, U.S. Prov. App. No. 62/755,365, which are fully incorporated by reference herein.

Also described herein is a method of diagnosis, including assaying one or more biomarkers in a subject suspected of being afflicted with Parkinson's Disease, comparing the expression levels of the one or more biomarkers from the subject to a baseline of the one or more biomarkers derived from healthy subjects without Parkinson's disease, and diagnosing Parkinson's Disease in the subject.

Also described herein is a method of prognosis, including assaying one or more biomarkers in a subject suspected of being afflicted with Parkinson's Disease, comparing the expression levels of the one or more biomarkers from the subject to a baseline of the one or more biomarkers derived from healthy subjects without Parkinson's disease, and prognosing Parkinson's Disease in the subject.

Further described herein is a method of selecting a therapeutic regimen, including assaying one or more biomarkers in a subject suspected of being afflicted with Parkinson's Disease, comparing the expression levels of the one or more biomarkers from the subject to a baseline of the one or more biomarkers derived from healthy subjects without Parkinson's disease, and selecting a therapeutic regimen for the subject.

In various methods for prognosis, diagnosis, or aiding therapeutic selection, the biomarker is a metabolic enzyme, including neurotransmitters such as dopamine. In various embodiments, biomarkers include α-synuclein expression levels, including transcript and protein levels. In various embodiments, biomarker include PKC activation. In other embodiments, the biomarkers include at least one of TFEB activation and ZKSCAN3 inactivation. In other embodiments, the one or more parameters comprise α-synuclein protein levels. In other embodiments, the biomarkers include at least one of: LAMP1, GCase, tyrosine hydroxylase (TH), and dopaminergic activity. In other embodiments, the biomarkers include at least one of: LAMP, GCase, tyrosine hydroxylase (TH) and dopamine expression levels. In various embdoiments, the biomarkers include markers of aberrant protein degradation, such as lysosomal dysfunction. In various embodiments, the biomakers include nestin, Tuj1, MAP2, GFAP, S100B, CD11B, PU.1, GLUTA-1, ZO-1, SMI31/Isl1, TH/PITX3, Phospho-TDP, FAS ligand, and SOD1, among others.

In various embodiments of the aforementioned, neurodegenerative disease derived induced pluripotent stem cells (iPSCs) and differentiated cells thereof possess a molecular signature different from iPSCs derived from healthy controls. In various embodiments, the molecular signature includes difference in metabolic pathways and metabolites. For example, this includes metabolites such as, for example, enrichment in one or more of L-Kynurenine, trans-aconitic acid, adenine, inosine, and 1-tyrosine.

Described herein is a method of cryopreservation of differentiated iPSCs. In various embodiments, the differentiated iPSCs are treated with a culture media, treated with a proteolytic and collagenolytic agent, placing the differentiated iPSCs in a cryoprotective agent, exposing the differentiated iPSCs to an initiation temperature, cooling the differentiated iPSCs, supercooling the differentiated iPSCs to a solid phase, heating the differentiated iPSCs, and reducing the temperature of the differentiated iPSCs solid phase. In other embodiments, the cryoprotective agent includes serum. In other embodiments, the initiation temperature is about −4° to about 40° C. In other embodiments, the initiation temperature is about 2° to about 20° C. In other embodiments, the initiation temperature is about −1° to about 15° C. In other embodiments, the initiation temperature is about 3° to about 7° C. In other embodiments, cooling the differentiated iPSCs includes reaching a temperature of about −5 to −15° C. In other embodiments, cooling the differentiated iPSCs includes reaching a temperature of about −3 to −7° C. In other embodiments, cooling the differentiated iPSCs includes reaching a temperature of about −5° C. In other embodiments, supercooling the differentiated iPSCs includes reaching a temperature of about −20 to −90° C. In other embodiments, supercooling the BMECs includes reaching a temperature of about −40 to −75° C. In other embodiments, supercooling the differentiated iPSCs includes reaching a temperature of about −58° C. In other embodiments, supercooling is at a rate of about −20 TO −60° C./minute. In other embodiments, supercooling is at a rate of about −45° C./minute. In other embodiments, heating the differentiated iPSCs includes reaching a temperature of about −23° C. In other embodiments, heating the differentiated iPSCs is at a rate of about +10° C./minute to about −26° C. and/or +3° C./minute to about −23° C. In other embodiments, reducing the temperature of the differentiated iPSCs solid phase includes reaching a temperature of about −30° C. to about −50° C. In other embodiments, reducing the temperature of the differentiated iPSCs solid phase includes reaching a temperature of about −40° C. In other embodiments, reducing the temperature of the differentiated iPSCs solid phase is at a rate of about −3 to −0.05° C./minute. In other embodiments, reducing the temperature of the differentiated iPSCs solid phase is at a rate of about −0.8° C./minute. In other embodiments, rapid cooling of the reduced temperature differentiated iPSCs solid phase at a rate of about −10° C./minute to about −100° C. and/or about −35° C./minute to about −160° C. In other embodiments, the method includes transfer of the differentiated iPSCs to liquid nitrogen. In various embodiments, the culture media is neuron maturation media. In various embodiments, the culture media includes a ROCK inhibitor. In various embodiments, the proteolytic and collagenolytic agent is accutase.

In various embodiments, the differentiated iPSCs are midbrain neurons. In various embodiments, the differentiated iPSCs are floorplate cells. In various embodiments, the differentiated iPSCs produce tyrosine hydroxylase and/or or dopamine. In various embodiments, the differentiated iPSCs express higher levels of α-Synuclein compared to controls derived from healthy subjects. In various embodiments, the differentiated. iPSCs exhibit abnormal protein degradation, including lysosomal dysfunction. In various embodiments, the differentiated cells exhibit abnormal levels or activity of LAMP1 and/or Gcase. Described herein is a cryopreserved solution of differentiated cells prepared by the aforementioned methods.

EXAMPLE 1

Generation of iPSCs from Early Onset Sporadic Parkinson's Disease Patients (EO-sPD)

Three early onset sporadic Parkinson's patients between the ages of 30-39 with no reported family history of PD were selected for iPSC production (FIG. 1). Based on analysis with the NeuroX platform, no monogenic mutations in EIFG1, PARK2, LRRK2, GBA, SNCA, PINK1, PARK7, VSP35, ATP13A2 or multiplications of the SNCA locus were detected in the patient lines. All 3 patients demonstrated reduced DAT (phenyltropane) signature in the striatum consistent with their PD diagnosis (FIG. 1). For comparison, 3 control lines were generated from normal individuals with no neurological disease at time of collection.

Peripheral blood mononuclear cells (PBMCs) were collected and subsequently reprogramed to iPSCs using non-integrating episomal techniques (FIG. 1). All iPSC lines were karyotypically normal, and expressed canonical pluripotency markers.

EXAMPLE 2

Figure 2:
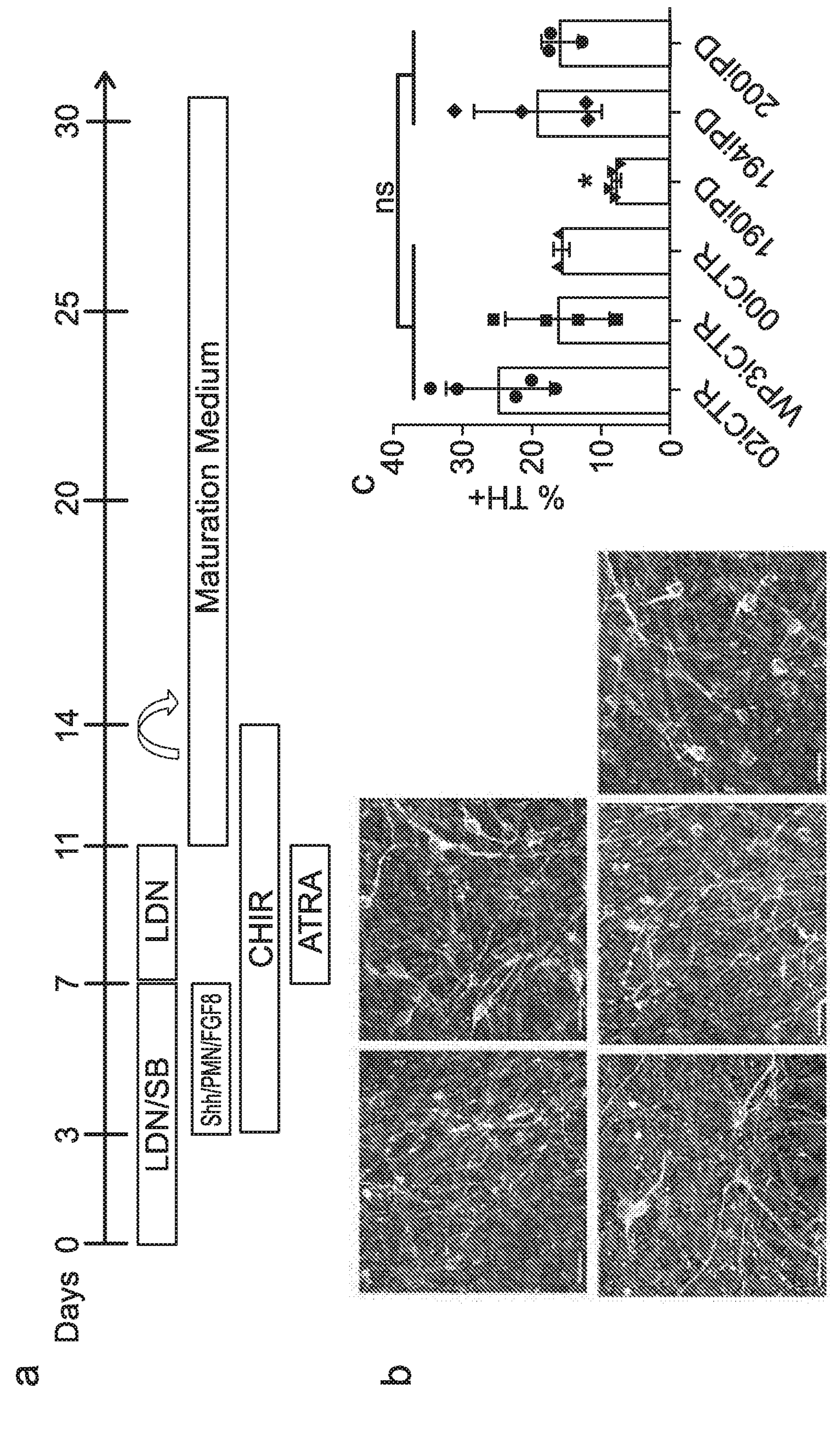
FIG. 2: Differentiation schematic (a). representative images showing TH expression and morphology (b) Flow cytometry data showing differentiation efficiency, each point represents an average of 3 separate wells of an independent differentiation (c). HLPC detection of total dopamine content (d) and dopamine content normalized to differentiation efficiency by line (e). Western blot showing bACT (housekeeping) and synuclein expression in 30 day old DaNs (f). Relative intensities from multiple western blots, each point is a band from a separate differentiation, colors indicate ipsc lines, data were normalized to 02iCTR for each differentiation (g). SNCA expression by qPCR in 30 day old DaNS (h).
Figure 2:
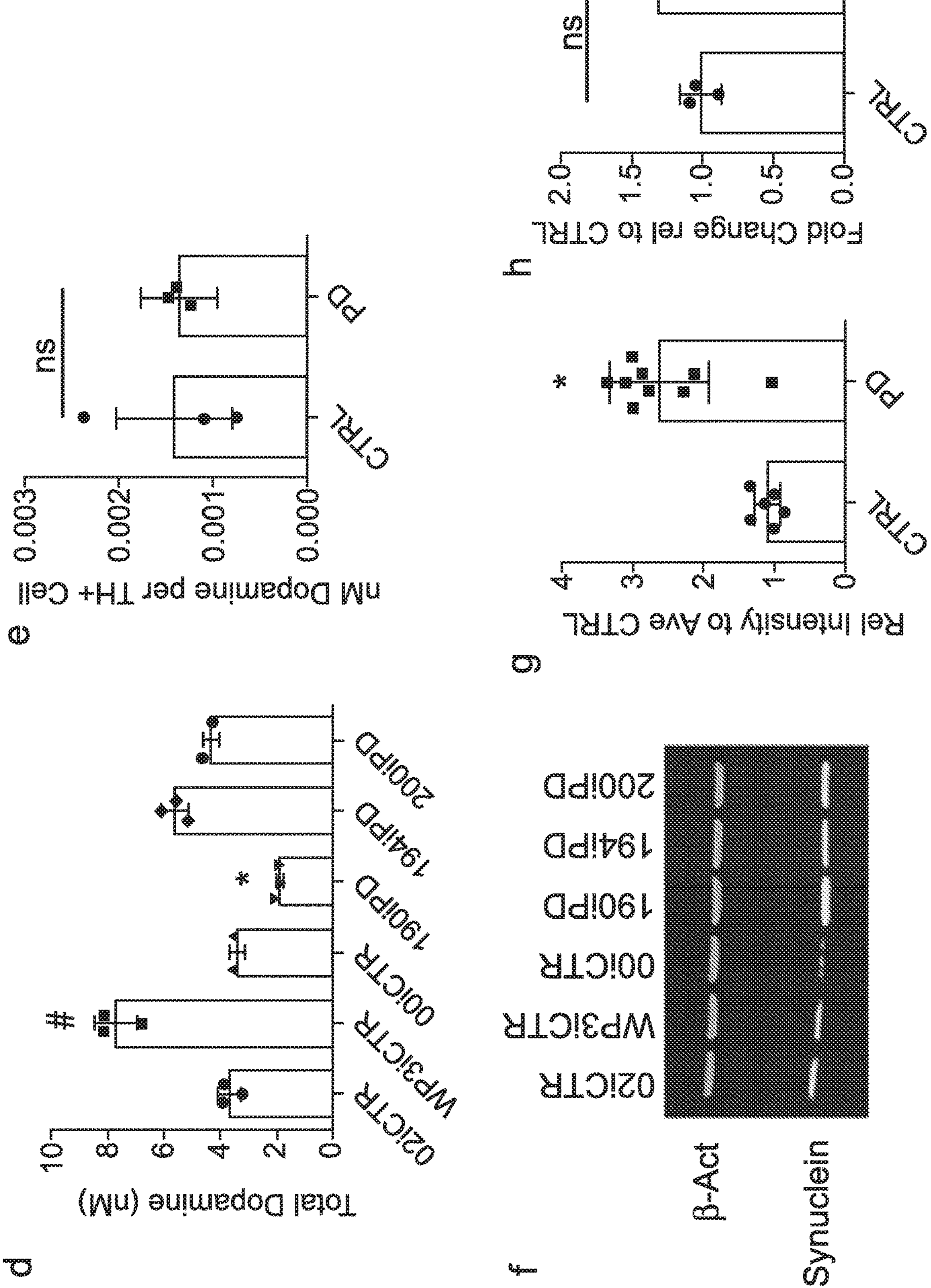
Figure 6:
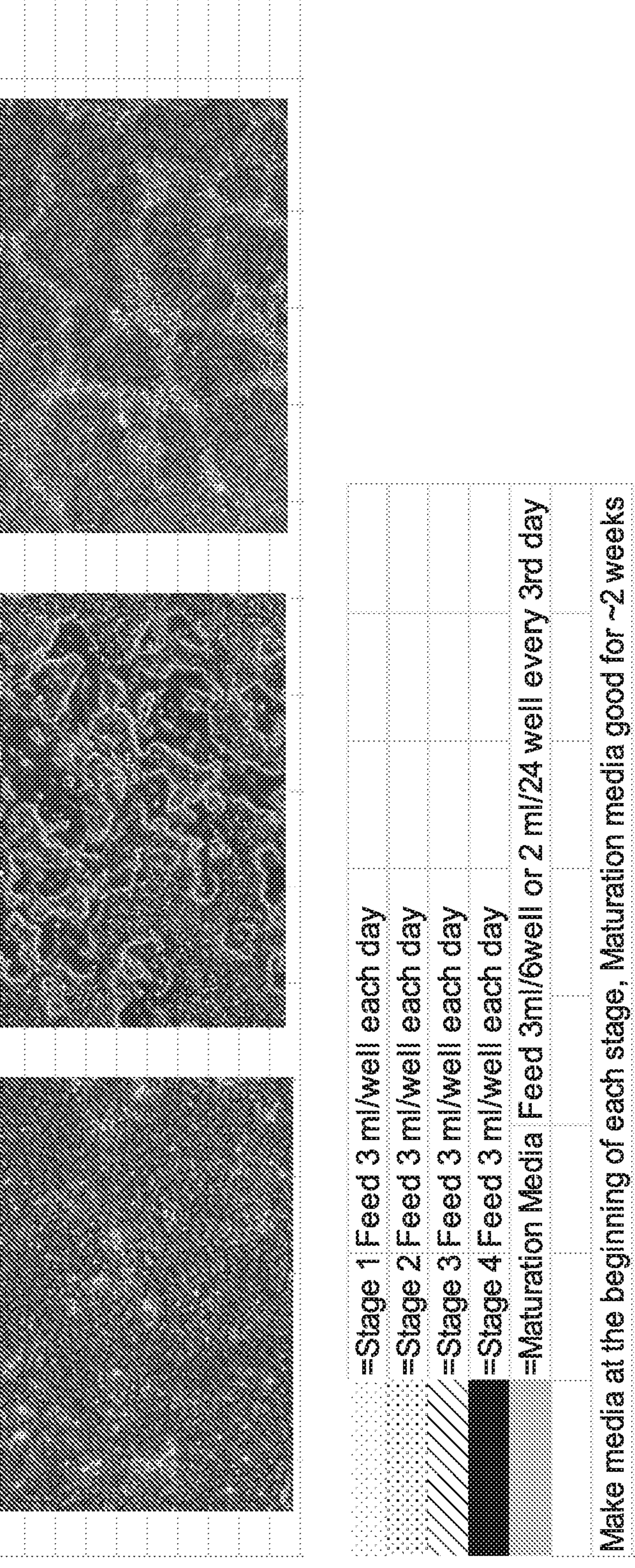
FIG. 6: Differentiation Protocol, including 4 stage time course (a) and maturation (b).
Figure 7:
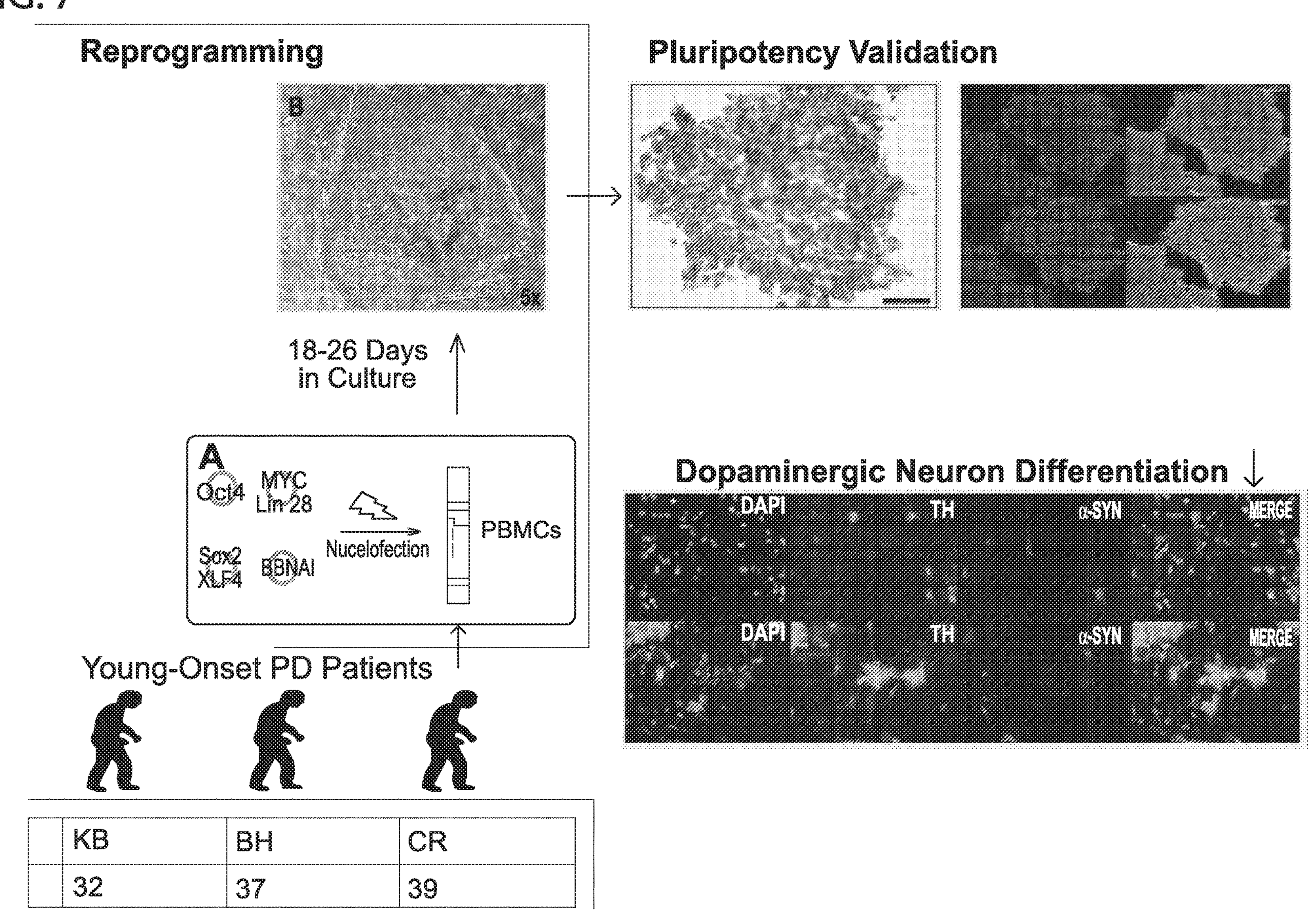
FIG. 7: Three patient volunteers exhibiting early onset of Parkinson's symptoms (confirmed by DaTscan) were evaluated at Cedars Sinai Medical Center. None of the patient's report family history of Parkinson's disease, indicating a sporadic disease origin. Detailed clinical evaluation and patient history data were recorded, and will continue to provide vital clinical information as disease modeling studies in vitro are carried out into the future. All three patients exhibit 1 on Hoehn and Yahr scale, indicating unilateral involvement and minimal functional disability.

Efficient Differentiation of EOSPD iPSCs to DANs A defining hallmark of PD is the specific loss of dopaminergic neurons in the substantia nigra and it is therefore of interest to differentiate iPSC along this lineage. iPSC lines from both PD and control patients were differentiated to dopaminergic neurons using the protocol described in Table 1, FIG. 2A and FIG. 6.

Briefly, iPSC lines were subjected to a modified dual SMAD-inhibition based floor plate induction protocol. Exposure to LDN/SB, followed by SHH/Purmorphamine/FGF8 and CHIR99021, thereafter including SB withdrawal and retinoic acid addition,support midbrain FP and DA neuron yield (see FIG. 1*d*). Further maturation was carried out in Neurobasal/B27 medium supplemented with AA, BDNF, GDNF, TGFβ3 and dbcAMP. The inclusion of retinoic acid, exclusion of retionoic acid from the early steps of differentiation are unlike any other known techniques. Remarkably, whereas reported protocols may take 80 to 130 days to produce a dopamine producing cells, the aforementioned techniques allow generation in as little as 30 days.

TABLE 1

Differentiation Protocol - Media

| Stage 1 Media: | | | | | for x volume |
|---|---|---|---|---|---|
| | Working Dilution | | | x= | 140 mL |
| DMEM/F12 | 50% | | | DMEM/F12 | 70 mL |
| Neurobasal | 50% | | | Neurobasal | 70 mL |
| N2 | 1:100 | | | N2 | 1.4 mL |
| B27 - Vitamin A | 1:50 | Stock: | Working: | B27 - Vitamin A | 2.8 mL |
| LDN | 1:10000 | 10 mM | 1 uM | LDN | 14 uL |
| SB | 1:5000 | 10 mM | 2 uM | SB | 28 uL |
| **Stage 2 Media:** | | | | | for x volume |
| | Working Dilution | | | x= | 220 mL |
| DMEM/F12 | 50% | | | DMEM/F12 | 110 mL |
| Neurobasal | 50% | | | Neurobasal | 110 mL |
| N2 | 1:100 | | | N2 | 2.2 mL |
| B27 - Vitamin A | 1:50 | | | B27 - Vitamin A | 4.4 mL |
| LDN | 1:10000 | | | LDN | 22 uL |
| SB | 1:5000 | Stock: | Working: | SB | 44 uL |
| PMN | 1:5000 | 10 mM | 2 uM | PMN | 44 uL |
| Shh | 1:1000 | 100 ug/mL | Shh | | 220 uL |
| CHIR | 1:6670 | 15 mM | 2.25 uM | CHIR | 33.00 uL |
| FGF8 | 1:5000 | 50 ug/mL | FGF8 | | 44 uL |
| **Stage 3 Media:** | | | | | for x volume |
| | | | | x= | 50 mL |
| DMEM/F12 | 50% | | | DMEM/F12 | 25 mL |
| Neurobasal | 50% | | | Neurobasal | 25 mL |
| N2 | 1:100 | | | N2 | 0.5 mL |
| B27 - Vitamin A | 1:50 | | | B27 - Vitamin A | 1 mL |
| LDN | 1:10000 | | | LDN | 5 uL |
| CHIR | 1:6670 | Stock: | Working: | CHIR | 7.50 uL |
| ATRA | 1:2000 | 10 mM | 5 uM | ATRA | 25 uL |
| **Stage 4 Media:** | | | | | for x volume |
| | | | | x= | 60 mL |
| DMEM/F12 | 50% | | | DMEM/F12 | 30 mL |
| Neurobasal | 50% | | | Neurobasal | 30 mL |
| N2 | 1:100 | | | N2 | 0.6 mL |
| B27 | 1:50 | Stock: | Working: | B27 | 1.2 mL |
| AA | 1:1000 | 500 ug/mL | AA | | 60.00 uL |
| BDNF | 1:500 | 10 ug/mL | 20 ng/mL | BDNF | 120.00 uL |
| GDNF | 1:500 | 10 ug/mL | 20 ng/mL | GDNF | 120.00 uL |
| dbCAMP | 1:500 | 102 mM | .2 mM | dbCAMP | 120.00 uL |
| TGF-B3 | 1:10000 | 10 ug/mL | 1 ng/mL | TGF-B3 | 6.00 uL |
| DAPT | 1:4000 | 10 mM | 2.5 uM | DAPT | 15.00 uL |
| CHIR | 1:6670 | | | CHIR | 9.00 uL |
| **Maturation Media:** | | | | | for x volume |
| | | | | x= | 100 mL |
| DMEM/F12 | 50% | | | DMEM/F12 | 50 mL |
| Neurobasal | 50% | | | Neurobasal | 50 mL |
| N2 | 1:200 | | | N2 | 0.5 mL |
| B27 | 1:100 | | | B27 | 1 mL |
| AA | 1:1000 | | | AA | 100.00 uL |
| BDNF | 1:500 | | | BDNF | 200.00 uL |
| GDNF | 1:500 | | | GDNF | 200.00 uL |
| dbCAMP | 1:500 | | | dbCAMP | 200.00 uL |
| TGF-B3 | 1:10000 | | | TGF-B3 | 10.00 uL |
| DAPT | 1:4000 | | | DAPT | 25.00 uL |

At day 30, differentiated cells expressed markers of dopamine neurons including TH, Nurr1, and GRIK2 with roughly 15% of the cells expressing TH (Supplemental FIG. 2*a*) (FIG. 2*b,c*). Overall differentiation efficiency was compared across all 6 lines by counting the number of TH expressing cells using flow cytometry (FIG. 2*c*). Two of the PD lines showed similar numbers of DA neurons to those found in controls. However, differentiation of the 190iPD line yielded fewer TH positive neurons and these cells expressed less of the floorplate progenitor markers FOXA2 and LMX1A but more of the mature neural markers GRIK2 and NEFH.

To determine whether TH enzyme resulted in altered levels of dopamine in the developing neurons, 30 day old DANs were lysed and analyzed for dopamine production by HPLC. Differences in total dopamine were present by line with the 190iPD line again producing less dopamine and the WP3iCTR line producing more. However, when normalized to the number of TH expressing neurons, all lines produced dopamine at similar levels (FIG. 2*d,e*). To determine the electrophysiological function and potential disease signature of the developing neurons, multi-electrode array recordings were conducted over time in culture. Spontaneous activity was observed day 20 of differentiation and by day 30, both PD and control cells produce coordinated bursts of activity. When activity was quantified across all lines, similar levels of spontaneous spikes were observed between disease and control DaN cultures. Together, these data indicate that iPSCs derived from EOSPD patients differentiated efficiently into functional dopaminergic neurons that possessed similar neural activity to non-diseased patient lines.

EXAMPLE 3

α-Synuclein Accumulates Specifically in EOSPD DANs

The protein α-Synuclein abnormally accumulates within Lewy bodies in all forms of Parkinson's disease, and accumulation through duplication or triplication of the SNCA gene is known to lead to PD. However, it's exact role in sporadic PD remains uncertain and previous studies have not shown consistent differences in adult onset sporadic PD. To determine if α-Synuclein protein accumulated the cultures of early onset sporadic PD origin, the 6 lines were differentiated for 30 days and probed for soluble α-Synuclein by western blot.

Strikingly, all 3 EOSPD DAN lysates exhibited increased levels of α-Synuclein protein when compared to controls (FIG. 2*f,g*). For verification of α-Synuclein accumulation, an ELISA was conducted on both media supernatant and cell lysates. The supernatant concentration of α-Synuclein was below detection limits, and cell lysates confirmed a significant increase in α-Synuclein protein in the diseased lines. Protein lysates from the lines at the iPSC stage did not exhibit increased α-Synuclein indicating accumulation was specific to the differentiated cultures.

To determine if the increased protein could be attributed to increased transcription of the SNCA gene, QPCR was conducted on DAN cultures at day 30 (FIG. 2*h*). These data indicate that two of the EOSPD lines, 190iPD and 200iPD, exhibit increased SNCA expression compared to the control lines but the third, 194iPD, does not suggesting that increased transcription alone was not the sole cause of α-Synuclein accumulation.

EXAMPLE 4

Lysosomal Proteins are Dysregulated in EOSPD DANs

Since increased transcription of the SNCA gene could not fully explain EOSPD specific α-Synuclein protein accumulation, the Inventors next sought to determine other factors that may contribute to this effect through both RNA sequencing and proteomics on a paired sample set derived from the same culture wells. Whole transcriptomic RNA sequencing (RNA-Seq) detected 27384 unique transcripts while proteomic analysis yielded 2478 proteins that met reproducibility thresholds. Pearson correlation coefficients showed high consistency among sample replicates.

Combinatorial analysis of proteins and transcripts common to both proteomics and RNA-Seq datasets yielded 2437 matched genes between the two analysis modes (FIG. 3*a*). Unsupervised principal component analysis (PCA) of the matched gene set revealed a clear delineation between the PD cells and control along PC1 from both transcriptomic and proteomic data sets (FIG. 3*b*). Analysis of the entire RNA-Seq dataset yielded similar PCA. To determine significant pathways that contributed to this separation, all matching genes were ranked by PC1 gene weighting from both the mRNA or proteomic PCA analysis. Separate GSEA analyses of each ranked list were then merged to reveal common pathways significantly dysregulated between the PD and control cells (FIG. 3*c*). α-Synuclein and other synaptic vesicle genes related to dopamine release such as Synapsin (SYP), synaptic vesicle 2 A (SV2A), and SNAP25 were significantly enriched in the term as well as terms related to general synaptic machinery and function such as GO_EXOCYTIC_VESICLE (FIG. 3*c*). Metabolic genes contained in KEGG_OXIDATIVE_PHOSPHORYLATION were also significantly upregulated in ESOPD lines. In addition, terms related to neurodegenerative disease such as PD, Alzheimer's, and Huntington's disease were significantly upregulated in PD DANs suggesting that important aspects of neurodegeneration had been captured in the culture system (FIG. 3*c*). Significantly downregulated terms GO_LYSOSOMAL_LUMEN and GO_ENDOPLASMIC_RETICULUM_LUMEN indicated deficiencies in proteogenesis and lysosomal protein degradation compared to non-diseased controls (FIG. 3*f*).

EXAMPLE 5

Degradation of α-Synuclein is Impaired in PD DANs

Figure 4:
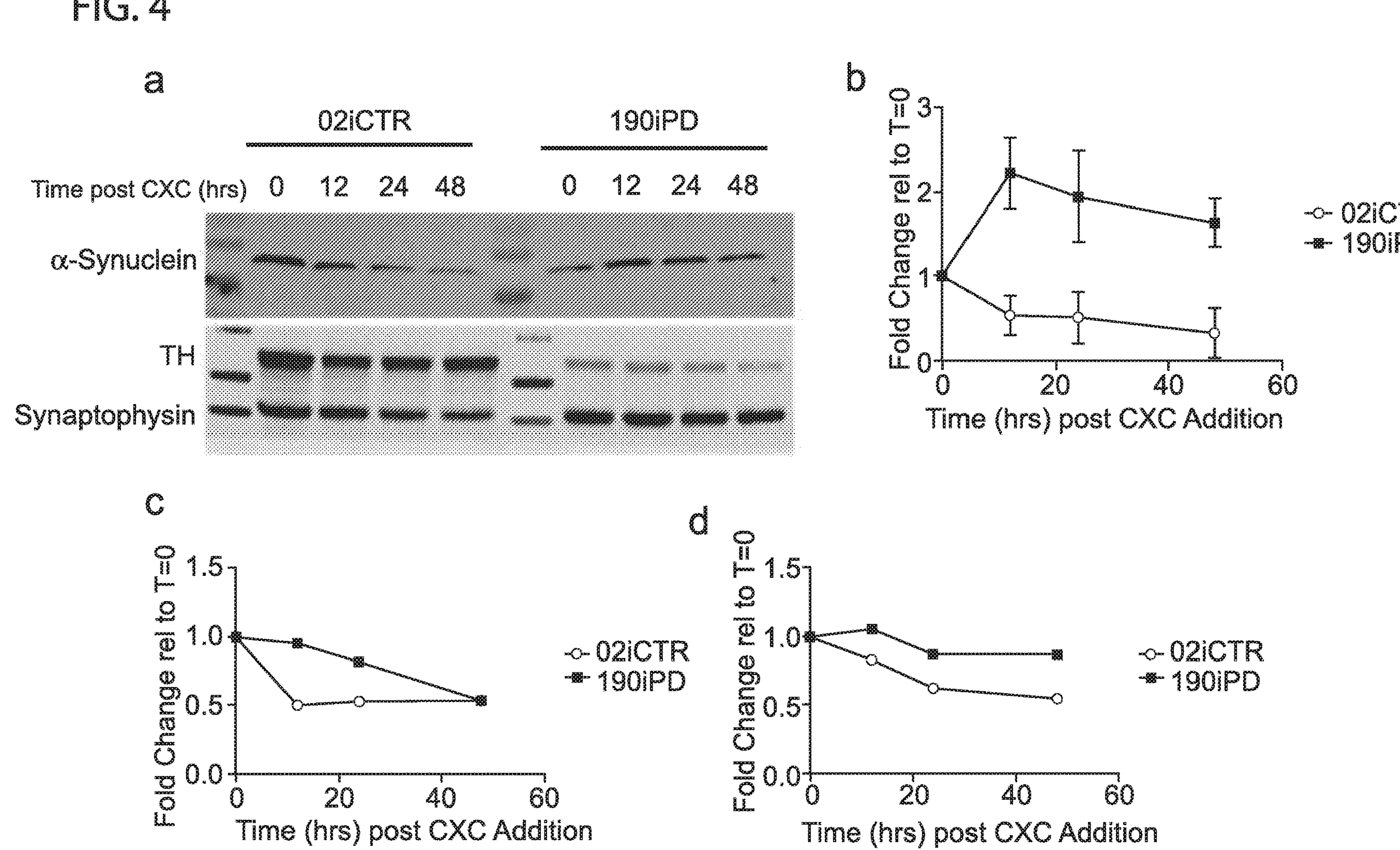
FIG. 4: representative western blot showing synuclein degradation under cycloheximide inhibition (a). average intensities of 3 separate differentiations and western blots from 02iCTR and 190iPD cells, presented as a fold change to time=0 synuclein (b), Synaptophysin (c), and TH (d). Western blot showing synuclein degradation under 24 hrs of MG132 proteosomal inhibitor (e). Western blot showing reduced LAMP1 protein in PD DaNs (f). GCase activity, each point is an average of 3 separate wells from a single differentiation. Data were normalized to 02iCTR for each differentiation and presented as a fold change (g). NIRF detection of oxidized dopamine from D30 DaN lysates (h)

Reduction in lysosomal proteins in EOSPD DANs led us to determine if accumulated α-Synuclein was the result of reduced degradation function. To test overall degradation rates, global transcriptional function was inhibited in DANs for 48 hours via cycloheximide treatment and α-Synuclein protein was quantified over time (FIG. 4*a,b*). In a control line, 02iCTR, α-Synuclein degraded over the course of the 48 hr treatment with an observed half-life of approximately 10 hours (FIG. 4*b*). However, in the most severe EOSPD line (190iPD) α-Synuclein instead accumulated over the duration of this treatment. This sharp dichotomy suggested fundamental deficiency in the specific degradation of α-Synuclein. This is supported by similar degradation profiles between control and PD cells of other proteins such as TH (FIG. 4*a,c*) and Synaptophysin (FIG. 4*a,d*).

Protein degradation can be largely divided into protosomal and autophagy/lysosomal degradation pathways. To determine proteosomal degradation was responsible for α-Synuclein proteolysis, DaN cultures were treated with the proteasome inhibitor MG132 for 24 hrs which resulted in accumulation of P53, a protein canonically degraded via proteosomal means, but no substantial change in α-Synuclein levels (FIG. 4*e*). This result indicates proteasome degradation was not a significant contributor to α-Synuclein degradation in DAN cultures.

To determine lysosomal involvement in α-Synuclein degradation, the Inventors probed for glucocerebrosidase or GCase activity and total LAMP1 protein. The Inventors observe a reduction in the amount of LAMP1 in all 3 EOSPD lines consistent with the proteomics analysis (FIG. 4*f*). GCase is a class of lysosomal hydrolases that have been reported as having reduced activity in peripheral blood of some PD patients. In 30 day old DaNs from EOSPD patients, significantly reduced GCase activity was observed compared to controls (FIG. 4*f*). Others have found that reduced GCase activity in iPSC derived DaNs was caused by an increase in oxidized dopamine. However, a similar increase in oxidized dopamine was not seen in our 30 day old PD DaNs (FIG. 4*h*). Taken with the significant downregulation of lysosomal pathway proteins, these results provided evidence of dysfunctional lysosomal degradation as the putative cause of α-Synuclein accumulation in EOSPD DANs.

EXAMPLE 6

Modulation of PKC Signaling Rescues EOSPD Phenotypes

Figure 5:
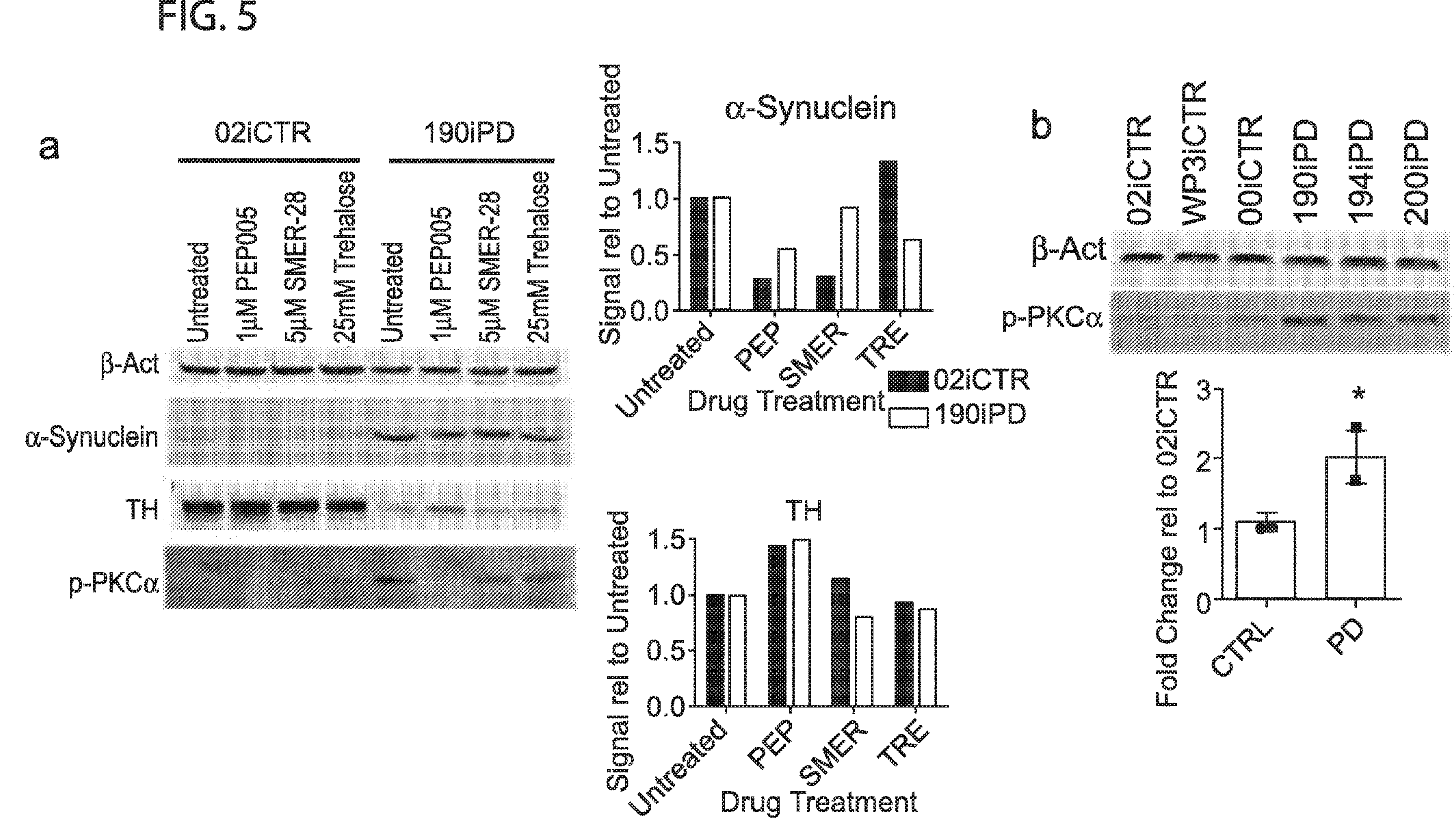
FIG. 5: Treatment with lysosomal agonists and Elevated p-PKCa in PD lines. Western blot and relative band quantifications of d30 DaNs treated with indicated compounds for 72 hours (a). Baseline levels of p-PKCa in d30 DaNs (b). Day 30 DaNs treated with PEP from multiple PD and control lines(c). Timecourse of PEP treatment and synuclein levels (d) Timecourse of PEP treatment SNCA (e) and TH (f) gene expression. Confirmation of elevated synuclein and p-PKCa in addition control and PD lines (g)
Figure 5:
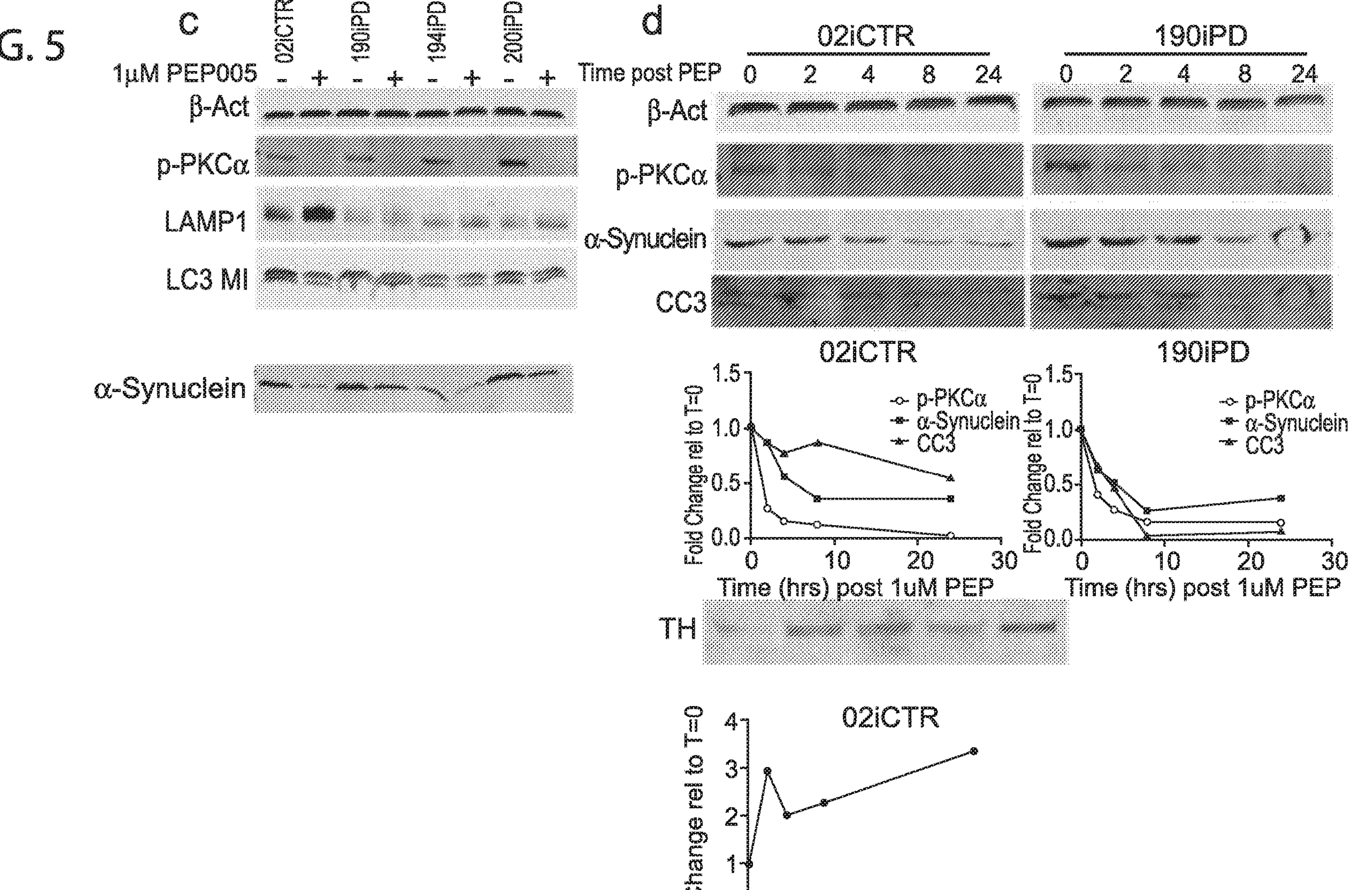

To test if the Inventors could reduce synuclein levels in our EOSPD DANs through activation of lysosomal specific pathways, the Inventors selected 3 lysosomal agonists. The compounds the Inventors selected were: PEP005, a PKC agonist and structural analogue of the HEP14 drug, SMER28, a small molecule TFEB agonist shown to reduce Huntington and α-Synuclein aggregates in a PC12 cell model, and Trehalose, another biological compound shown to promote clearance of α-Synuclein. Starting at day 27, DaNs were treated for 3 days with the above lysosomal agonists. Treatment with both PEP005 and SMER28, but not Trehalose significantly reduced the amount of α-Synuclein protein in DaNs from control lines (FIG. 5*a*). However, in ESOPD DaNs, only the PKC agonist PEP005 substantially reduced synuclein levels. Interestingly in both control and PD DaNs, PEP005 treatment also resulted in an increased amount of TH enzyme present (FIG. 5*a*).

The interesting combined effects of lowering synuclein levels in both control and PD DANs while simultaneously increasing TH expression in response to PEP005, led us to investigate the mechanism of action of the drug. PEP005 is an established PKC delta agonist that results in a short burst of PKC phosphorylation followed by a strong reduction in phosphorylated PKC over longer times. At endpoint in this study, the Inventors observed increased basal levels of PKC alpha phosphorylation in untreated 190iPD DaNs (FIG. 5*a*) with PEP005 treatment completely ablating this signal in both control and PD DaNs (FIG. 5*a, c*).

Having observed increases in phospho-PKCa at baseline in the 190iPD line, the Inventors checked all additional DANs to see if this observation was validated across multiple lines. The Inventors found higher levels of p-PKCa in 30 day DANs from all 3 EOSPD lines (FIG. 5*b*). The Inventors also checked 3 additional newly derived EOSPD lines (172iPD, 183iPD, 192iPD), 3 additional controls (0771iCTR, 1034iCTR, 1185iCTR), and a normal onset PD line (78iPD, age 67 @ onset, family history of PD) for both α-Synuclein accumulation and increased p-PKCa (FIG. 5*g*).

The elevated phosphorylation of PKCa was absent in the undifferentiated iPSCs and no clear pattern was evident in peripheral blood from the individual patients indicating specificity to the differentiated DaNs. Elevated phosphorylation of PKCa is clearly ablated by the addition of luM PEP005 for 3 days in DaNs from all iPSC lines (FIG. 5*c*). While this ablation does correlate with reduced synuclein in all treated lines it appears that neither LAMP1 nor LC3 respond to PEP treatment in PD cells (FIG. 5*c*) indicating that the mechanism of action in the PD cells may be different from a canonical upregulation of lysosomal proteins. A time-course of PEP treatment in control and PD DaNs shows that both p-PKCa and α-Synuclein are degraded in response to drug treatment within about 24 hrs (FIG. 5*d*). This same timecourse also shows a marked decrease in cleaved caspase 3 (CC3) present in the PD cells. Gene expression data from paired samples along this same timecourse indicates that SNCA is downregulated 4 hours after PEP treatment (FIG. 5*e*) and TH is upregulated roughly 8 hours after initial exposure (FIG. 5*f*).

EXAMPLE 7

In Vivo Reduction of α-Synuclein in WT Mice

In vivo, PEP stimulates synuclein degradation. Dosage studies of 0.3, 3, and 30 uM PEP was injected into the ventricles of WT mice. Reduction of synuclein and increase in TH in mouse striatum after 1 and 5 days post injection.

EXAMPLE 8

Discussion

The Inventors began this study looking for a signature of parkinsonism in dopaminergic neurons differentiated from early onset sporadic PD patient iPSCs. In a random selection of patients with an early onset and no family history of PD, the Inventors reprogrammed PBMCs from 3 individuals. The resulting iPSC lines were genetically normal and lacked many of the known monogenic PD mutations. The genomic chip assay used to assess this covers ~260,000 known SNPs associated with neurodegenerative disorders. It is possible, if highly unlikely, that the 3 idiopathic individuals used to generate the PD iPSCs all have as yet unknown monogenic mutations that were missed by the NeuroX screen. Regardless, the complex background genetics of these EOSPD iPSCs resulted in the accumulation of α-Synuclein in DaNs at only 30 days of age. This is the first identified phenotype in iPSCs derived from sporadic Parkinson's patients.

The Inventors then moved to complete an in depth analysis of these differentiated cells using both transcriptomic and proteomic techniques. Transcriptomic analysis revealed increased expression of many synaptic and exocytic transcripts in the PD cells. These increased transcripts also directly translated to elevated protein levels in the PD DaNs indicating an overabundance of synaptic machinery. However, despite the presence of more synaptic machinery, neither MEA recordings or live calcium imaging demonstrated a difference in activity between the PD and control DaNs. Conversely, the proteomics data indicate a reduction in the amount of lysosomal lumen proteins in PD DaNs. This decrease was not reflected in the RNA of the same cells which indicates a disconnect in this signaling pathway. There is less protein but the cells are not responding to make more. This reduction in lysosomal proteins is further confirmed by the reduced in GCase activity in PD DaNs, reduced LAMP1 protein by western blot, and the accumulation of α-Synuclein under cycloheximide inhibition, all of which point to some deficit in protein degradation in the PD DaNs. This deficit also seems to be specific to lysosomal degradation pathways as inhibition of proteosomal degradation did not result in any change in α-Synuclein levels.

The Inventors next selected a series of lysosomal agonists to attempt to correct this observed deficiency. Of the 3 tested agonists, only the PEP005 small molecule reduced α-Synuclein levels in both control and PD DaNs. Interestingly, PEP treatment also resulted in an increase in the amount of TH present in the treated cultures of both control and PD DaNs. The dual effects of reducing intracellular α-Synuclein levels and increasing TH observed here make PEP005 a very attractive candidate as a potential therapeutic agent.

PEP005 (ingenol-3-angelate) is an FDA approved drug for topical treatment of actinic keratinosis that also has anti leukemic activity and may play a role in reactivating latent HIV. Also known as ingenol-3-angelate and ingenol mebutate, it is the most studied ingenol derivative initially extracted from the sap of the plant *Euphorbia peplus*. This small molecule binds to the PKC C1 domains with subnanomolar affinity and shows no selectivity for individual PKC isoforms in vitro, although patterns of PKC isoform translocation and down-regulation induced by PEP005 can differ, sometimes in a cell line-dependent manner. It was selected in this study as a structural analogue derived from the same *Euphorbia peplus* plant as the HEP14 (5β-O-angelate-20-deoxyingenol) compound identified by Li and colleagues which acts as a TFEB agonist, independent of the MTOR pathway.

In control cells treated with PEP005, the Inventors observed an increase in the lysosomal protein LAMP1 consistent with activation of the lysosomal master regulator TFEB, but this increase does not appear to be replicated in the PD DaNs treated with the drug. PEP is described as both an activator of the pro-apoptotic PKC6 and an inhibitor of PKCα. PEP005 has been described as inhibiting proliferation of various cancer cell lines and primary acute myeloid leukaemia (AML) cells. In leukemic cell lines and primary AML cells, it induces apoptosis by activating PKCδ and by subsequently inducing sustained activation of ERK1/2.

In our DaN cultures, the Inventors did not observe a strong PKC6 signal nor do the Inventors see an increase in LDH on drug treatment as might be expected if the Inventors were inducing cell death. In fact, the Inventors observed a decrease in the amount of active caspase 3 on drug treatment, although this effect is most easily observed in the PD DaNs which have higher levels of cleaved caspase 3 to begin with. It is likely that the toxicity of PEP is more specific to highly proliferative cells whereas our differentiated neurons are largely post mitotoic.

In investigating the mechanism of action of the PEP005 small molecule in our DaNs, the Inventors observed increased levels of phosphorylated PKCa in the PD DaNs. It has been suggested that synuclein not only binds to and shares homology with the canonical 14-3-3 proteins involved with TFEB activation, but also binds PKCa, suggesting a link between our observed synuclein accumulation, lysosomal biogenesis, and the PKC agonist PEP005. PKC couples activation of the TFEB transcription factor with inactivation of the ZKSCAN3 transcriptional repressor through two parallel signalling cascades. Activated PKC inactivates GSK3, leading to reduced phosphorylation, nuclear translocation and activation of TFEB, while PKC phosphorylate ZKSCAN3, leading to its inactivation by translocation out of the nucleus. PKC activation may therefore mediate lysosomal adaptation to many extracellular cues, including clearance of aggregated proteins, thereby providing viable treatment options for disease and disorders with a lysosome nexus, such as the Parkinson's mechanism outlined here.

α-Synuclein degradation has been controversial, but it appears that the bulk of degradation of at least monomeric WT α-synuclein in neuronal cell systems occurs through the lysosomal pathways of chaperone-mediated autophagy (CMA) and macroautophagy. Dysfunction of these degradation pathways may be a contributing factor to PD pathogenesis Here, targeting of PKC demonstrates the viability of strategies directed toward promoting endogenous degradation systems to enhance clearance of excess α-synuclein, and can have the advantage that they could also alleviate the aberrant effects of α-synuclein on their function This work is the first to identify a molecular signature of sporadic Parkinson's disease in iPSCs from early onset patients. The Inventors find that these cells accumulate α-Synuclein, have dysregulated lysosomal biogenesis and function, and also display more heavily phosphorylated PKC alpha. Taken together these three biomarkers give us a platform to screen for new therapeutic agents that may impact the underlying mechanisms in PD. The Inventors went on to identify a novel drug in PD that eliminates this signature and reduces intracellular α-Synuclein in both control and PD cells. These findings implicate a specific and novel drugable pathway that presents an opportunity to finally treat some of the underlying mechanisms of PD.

EXAMPLE 9

Freezing Protocol

The Inventors developed a cryopreservation technique for dopaminergic neuron cells. Such technique allows preparation of cells for the aforementioned screening techniques and other applications.

Freezing Protocol:

Day 14 of DA neuron (midbrain culture) protocol:

1. Treat cultures with DA neuron maturation media (DAN MAT)+ROCKi (1:1000) for 30 minutes.
2. While treating, thaw accutase at RT, place on ice.
3. Replace ROCKi DAN MAT with accutase and incubate at 37C for 20-30 mins (until cells lift).
4. Add 3 ml of stage DAN MAT to each well and remove cells, place into 15 ml conical tube.
5. Spin down cells at 1060RPM (300g) for 5 minutes.
6. Remove supernatant and replace with Cold CryoStor storage media.
7. Use control rate freezer using standard supercooling protocol.

Thawing Protocol:

1. Remove vial from LN2 and store on dry ice until thawing.
2. Place into water bath and move in FIG. 8 until almost completely thawed.
3. Using P1000, Remove all cells from vial and place into 15 ml conical. No more than two vials per conical.
   a. slowly triturate about 300 ul back out ONCE and recollect to dislodge any cells stuck to bottom of vial.

4. Once all vials are in conical, add 1:1 vol:vol DAN maturation media (DAN MAT) to all conicals and shake together to insure mixing.
   a. Example: if 1 vial added at 500 ul, then add 500 ul DAN MAT. If 2 vials totaling lml cells, add lml DAN MAT.
5. Return to each conical and add 1:2 vol:vol, repeat mixing, be careful that the tip of the concial is mixed, but this should not take longer than 15 seconds.
   a. Example: if 1 vial, now add lml.
6. Finally, add 1:2 vol:vol of DAN MAT. Replace all caps and invert ONCE. Place in centrifuge and spin down 1060RPM for 5 mins.
   a. Example: if 1 vial, now totaling 2 ml, add 4 ml for a total of 6 ml.
7. Remove supernatant and resuspend with desired volume of DAN MAT +ROCKi (1:2000).
8. Seeding density must be high (300,000 for 96 well plate, or 12E6/ml for Chip)

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions and methods related to induced pluripotent stem cells (iPSCs), differentiated iPSCs including midbrain neurons, floorplate neurons, dopaminergic neurons, methods and compositions related to use of the aforementioned compositions, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of screening one or more test compounds for treating early onset sporadic Parkinson's Disease, the method comprising:

contacting a quantity of midbrain dopaminergic neurons differentiated from early onset sporadic Parkinson's Disease patient blood cell-derived induced pluripotent stem cells (iPSCs) with the one or more test compounds;

measuring a-synuclein protein levels and PKCα phosphorylation levels in the contacted midbrain dopaminergic neurons; and selecting one or more of the test compounds as a compound or compounds for treatment of early onset sporadic Parkinson's Disease based on the measured a-synuclein protein levels and PKCα phosphorylation levels, the selected one or more compounds being able to reduce α-synuclein protein levels and PKCα phosphorylation levels in the midbrain dopaminergic neurons, compared to α-synuclein protein levels and PKCα phosphorylation levels in the dopaminergic neurons not contacted with the selected one or more compounds, wherein the iPSCs are produced from early onset sporadic Parkinson's Disease patients who are younger than 50 years old with no reported family history of Parkinson's Disease, wherein the midbrain dopaminergic neurons express higher levels of α-synuclein and phosphorylated PKC-α compared to controls derived from healthy subjects.

2. The method of claim 1, further comprising measuring at least one of transcription factor EB (TFEB) activation and zinc finger with KRAB and SCAN domains 3 (ZKSCAN3) inactivation in the contacted midbrain dopaminergic neurons.

3. The method of claim 1, further comprising measuring dopaminergic activities or dopamine level in the contacted midbrain dopaminergic neurons.

4. The method of claim 1, further comprising measuring tyrosine hydroxylase (TH) activity in the contacted midbrain dopaminergic neurons.

5. The method of claim 1, further comprising measuring tyrosine hydroxylase (TH) levels in the contacted midbrain dopaminergic neurons.

6. The method of claim 1, further comprising measuring lysosomal associated membrane protein (LAMP) 1 expression level, GCase activity, and GCase expression level in the contacted midbrain dopaminergic neurons, wherein the compound is or the compounds are selected when decreased α-synuclein protein levels, decreased PKCα phosphorylation levels, increased LAMP 1 expression level, increased GCase activity, and increased GCase expression level are detected, wherein the midbrain dopaminergic neurons express higher levels of a-synuclein and phosphorylated PKCα and lower levels of LAMP1 expression, GCase activity, and GCase expression compared to control derived from healthy subjects.

7. The method of claim 1, wherein the blood cell-derived iPSCs are made by a method comprising:

contacting a quantity of blood cells with one or more oriP/EBNA1 vectors encoding a reprogramming factor;

delivering a quantity of reprogramming factors into the blood cells; and culturing the blood cells in a reprogramming media, wherein delivering the reprogramming factors and culturing in the reprogramming media generate blood cell-derived iPSCs.

8. The method of claim 7, wherein the quantity of blood cells is obtained from the early onset sporadic Parkinson's Disease patients who are younger than 50 years old with no reported family history of Parkinson's Disease.

9. The method of claim 1, wherein the neurons are differentiated from blood cell-derived iPSCs by a method comprising:

providing a quantity of blood cell-derived induced pluripotent stem cells (iPSCs);

culturing the iPSCs in the presence of a transforming growth factor (TGF)-beta inhibitor and an activin receptor-like kinase (ALK) inhibitor;

culturing the iPSCs in the presence of a Smoothened agonist, a RHO Kinase (ROCK) inhibitor and at least two growth factors;

culturing the iPSCs in the presence of retinoic acid; and culturing the iPSCs in the presence of at least three additional growth factors.

10. The method of claim 9, wherein the transforming growth factor (TGF)-beta inhibitor comprises LDN-193189 and the activin receptor-like kinase (ALK) inhibitor comprises SB431542, the Smoothened agonist comprises Purmorphamine, the at least two growth factors comprise sonic hedgehog and fibroblast growth factor 8, the ROCK inhibitor comprises CHIR99021, and the at least three additional growth factors comprise brain derived neurotrophic factor, glial derived neurotrophic factor, and TGF-Beta 3.

* * * * *